(12) United States Patent
Moturu et al.

(10) Patent No.: US 10,276,260 B2
(45) Date of Patent: Apr. 30, 2019

(54) METHOD FOR PROVIDING THERAPY TO AN INDIVIDUAL

(71) Applicant: Ginger.io, Inc., San Francisco, CA (US)

(72) Inventors: Sai Moturu, San Francisco, CA (US); Anmol Madan, San Francisco, CA (US); Karan Singh, San Francisco, CA (US); Abhishek Nath, San Francisco, CA (US); Amanda Withrow, San Francisco, CA (US); Aditya Sharma, San Francisco, CA (US)

(73) Assignee: Ginger.io, Inc., San Francisco, CA (US)

( * ) Notice: Subject to any disclaimer, the term of this patent is extended or adjusted under 35 U.S.C. 154(b) by 373 days.

(21) Appl. No.: 15/005,923

(22) Filed: Jan. 25, 2016

(65) Prior Publication Data

US 2016/0140320 A1 May 19, 2016

Related U.S. Application Data

(63) Continuation-in-part of application No. 13/969,339, filed on Aug. 16, 2013.
(Continued)

(51) Int. Cl.
*G16H 10/20* (2018.01)
*G06F 19/00* (2018.01)
(Continued)

(52) U.S. Cl.
CPC .......... *G16H 10/20* (2018.01); *G06F 19/00* (2013.01); *G06F 19/3418* (2013.01);
(Continued)

(58) Field of Classification Search
None
See application file for complete search history.

(56) References Cited

U.S. PATENT DOCUMENTS

| 4,845,323 A | 7/1989 | Beggs |
| 6,356,940 B1 | 3/2002 | Short |

(Continued)

FOREIGN PATENT DOCUMENTS

| CN | 101600008 A | 12/2009 |
| WO | 2008085308 A1 | 7/2008 |

(Continued)

OTHER PUBLICATIONS

"Major Virginia Smith; et al. 'Work Time Interference With Family, and Psychological Distress' 2002, Journal of Applied Psychology, vol. 87, No. 3, 427-436 (Year: 2002)", Jan. 11, 2018 00:00:00.0.

*Primary Examiner* — Michael Tomaszewski
(74) *Attorney, Agent, or Firm* — Jeffrey Schox

(57) ABSTRACT

A method and system for providing therapy to an individual, the method comprising: transmitting a log of use dataset associated with communication behavior of the individual during a time period; receiving a supplementary dataset characterizing mobility of the individual in association with the time period; generating a survey dataset upon retrieving responses provided by the individual to at least one of a set of surveys, associated with a set of time points of the time period; generating a predictive model from a passive dataset derived from the log of use dataset and the supplementary dataset and the survey dataset; generating a report summarizing a mental health state of the individual, associated with at least a portion of the time period, from the passive dataset, the survey dataset, and an output of the predictive model; and rendering information from the report to a coach associated with the individual.

23 Claims, 23 Drawing Sheets

Related U.S. Application Data

(60) Provisional application No. 62/107,292, filed on Jan. 23, 2015, provisional application No. 61/683,867, filed on Aug. 16, 2012, provisional application No. 61/683,869, filed on Aug. 16, 2012.

(51) Int. Cl.
    *G09B 7/06*     (2006.01)
    *G16H 50/30*     (2018.01)
    *G16H 15/00*     (2018.01)
    *G16H 50/70*     (2018.01)
    *G16H 50/20*     (2018.01)

(52) U.S. Cl.
    CPC .......... *G06F 19/3481* (2013.01); *G09B 7/06* (2013.01); *G16H 15/00* (2018.01); *G16H 50/30* (2018.01); *G16H 50/20* (2018.01); *G16H 50/70* (2018.01)

(56) References Cited

U.S. PATENT DOCUMENTS

| | | | |
|---|---|---|---|
| 6,827,670 B1 | 12/2004 | Stark et al. | |
| 7,188,151 B2 | 3/2007 | Kumar et al. | |
| 7,248,677 B2 | 7/2007 | Randall et al. | |
| 7,337,158 B2 | 2/2008 | Fratkina et al. | |
| 7,376,700 B1 | 5/2008 | Clark et al. | |
| 7,761,309 B2 | 7/2010 | Sacco et al. | |
| 7,818,185 B2 | 10/2010 | Bjorner et al. | |
| 8,265,955 B2 | 9/2012 | Michelson et al. | |
| 8,398,538 B2 | 3/2013 | Dothie et al. | |
| 8,684,922 B2 | 4/2014 | Tran | |
| 8,726,195 B2 | 5/2014 | Bill | |
| 9,286,442 B2 | 3/2016 | Csoma et al. | |
| 2004/0225340 A1 | 11/2004 | Evans | |
| 2005/0108051 A1 | 5/2005 | Weinstein | |
| 2007/0094048 A1* | 4/2007 | Grichnik | G06Q 50/22 705/2 |
| 2007/0226012 A1 | 9/2007 | Salgado et al. | |
| 2007/0288266 A1 | 12/2007 | Sysko et al. | |
| 2009/0125333 A1 | 5/2009 | Heywood et al. | |
| 2010/0082367 A1* | 4/2010 | Hains | G06F 19/3456 705/2 |
| 2010/0179833 A1 | 7/2010 | Roizen et al. | |
| 2010/0203876 A1 | 8/2010 | Krishnaswamy | |
| 2010/0280838 A1 | 11/2010 | Bosworth et al. | |
| 2011/0009715 A1 | 1/2011 | Karplus et al. | |
| 2011/0066036 A1 | 3/2011 | Zilca et al. | |
| 2011/0184250 A1 | 7/2011 | Schmidt et al. | |
| 2012/0143013 A1 | 6/2012 | Davis, III et al. | |
| 2012/0221357 A1 | 8/2012 | Krause et al. | |
| 2013/0041290 A1 | 2/2013 | Kording et al. | |
| 2013/0117040 A1 | 5/2013 | James et al. | |
| 2013/0297536 A1* | 11/2013 | Almosni | G16H 50/20 706/12 |
| 2014/0039914 A1 | 2/2014 | Dansereau et al. | |

FOREIGN PATENT DOCUMENTS

| | | |
|---|---|---|
| WO | 2008096634 A1 | 8/2008 |
| WO | 2012025622 A2 | 3/2012 |
| WO | 042116 | 3/2013 |
| WO | 2015003247 A1 | 1/2015 |

\* cited by examiner

| Coach ID | User ID | User Name | Current PHQ-9 | PHQ-9 Time | Depression Trend | Coach Engmt | Last Coach Rating | Therapist Engmt | Last Therapist Rating | App Engmt | Passive Prediction | Escalation State | Risk Factors | Active Outreach Reco |
|---|---|---|---|---|---|---|---|---|---|---|---|---|---|---|
| 36 | 97 | Nancy N | 13 | 7D | ↓ | 16D | ↔ | Never | NA | 2D | ↓ | Coach | Poor Sleep, Subs Abuse | Yes |
| 36 | 113 | Carrie C | 17 | 9D | ↓ | 7D | ↓ | 3D | ↓ | 5D | ? | Therapy | High PHQ-9, Suic. Ideas | Yes |

State
↑ Improving
↔ Similar
↓ Worsening
? Unclear

FIGURE 10A

Coach C
Online

| Current | Outreach | Starred | All |

| ID | SI | OR | Msg | Last ▲ |
|---|---|---|---|---|
| 934 | 1 | P1 | 3 | Now |
| 1275* | 2 | P2 | 2 | 13m |
| 346 | 1 | | 1 | 67m |
| 761* | | P3 | | 2h |

SI: Suicidal Ideation
OR: Outreach Priority
Msg: Unread message count
Last: Time since last message

USER LIST VIEW
FIGURE 10B

Personal

61 yo, Male, not Hispanic/Latino separated, 1 child self-employed

History medical Hx: cancer, arthritis, substance abuse previous depression Dx: Yes substances: none family Hx: no known parental depression

Assessment

*[PHQ9 Trend chart]*

In the past 2 weeks

| | |
|---|---|
| Changes in Sleep | YES (sleeping more than normal) |
| Loss of Interest in activities | YES |
| Feelings of Guilt or Worthlessness | YES (worthlessness) |
| Lack of Energy | NO |
| Reduction in Cognition or Concentration | YES |
| Changes in Appetite or Weight Loss | NO |
| Psychomotor Agitation or Retardation | NO |
| Suicide or Death Preoccupation | YES (thoughts) |

Anti-Depressants
Wellbutrin, 4+ weeks
reported side effects: none

Ginger.io Notes[1]
- For suicidal thoughts, recommend local & national hotline resource 1-800-273-8255.
- Assess for suicidality
- John has been diligently tracking his mood on Ginger.io. His PHQ9 scores have been trending slightly down since June 2015, although still moderately severe.
- Continue follow up every 2-6 weeks and consider modifying or augmenting treatment to achieve remission goals.

Message to the Physician

FIGURE 12B

METHOD FOR PROVIDING THERAPY TO AN INDIVIDUAL

CROSS-REFERENCE TO RELATED APPLICATIONS

This application is a continuation-in-part application of U.S. application Ser. No. 13/969,339 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

This application also claims the benefit of U.S. Provisional Application Ser. No. 62/107,292 filed 23 Jan. 2015, which is incorporated in its entirety herein by this reference.

TECHNICAL FIELD

This invention relates generally to the field of psychological health and more specifically to a new and useful method for providing therapy to an individual in the field of psychological health.

BACKGROUND

Life event triggers and other factors contributing to adverse psychological states can result in a combination of symptoms that interfere with a person's ability to work, sleep, study, eat, and enjoy once-pleasurable activities. Changes in psychological state for a person can be triggered by or attributed to one or many factors, including relationship factors in one's personal life, changes in one's physical health, changes in one's diet, and changes in one's substance use. For some individuals diagnosed with a disorder or a condition, access to therapy, upon experiencing an adverse psychological state, can be as simple as making an appointment with a therapist or calling a friend, given familiarity with procedures for seeking help to improve one's state. However, for individuals experiencing a rare adverse state (e.g., due to loss of a loved one), undiagnosed individuals, and even some diagnosed individuals, seeking therapeutic measures that would improve psychological state can be an uncomfortable process, due to unfamiliarity with procedures for seeking help, social barriers to seeking help, difficulties in sharing sensitive information with a known entity, cost, limited availability of help (e.g., in the form of therapists), and other factors. In one example, a person who has experienced a breakup may feel some aversion to reaching out to friends or loved ones for help, thus prolonging the adverse state induced by the breakup.

Unfortunately, current standards of detection and treatment of adverse states in a wider population of individuals are extremely limited, which cause adverse states to linger and remain untreated. For instance, after an incident (e.g., a suicide, a violent incident, a death) has occurred within a school setting, hotlines are typically made available to individuals affected by the incident. However, adoption of such hotlines by affected individuals is typically low due to one or more of the factors described above. Furthermore, changes in an individual's state can often go undetected by the individual's peers, due to behaviors by the individual that hide the true state of the individual. Furthermore, methods of supporting individuals, reaching out to individuals suffering from an adverse mental condition, and/or triaging individuals in terms of escalating them to a point of clinical or therapeutic intervention are deficient. In addition to these deficiencies, further limitations in detection, treatment, and/or monitoring of progress post-treatment prevent adequate care of individuals whose psychological states could be improved by therapy.

As such, there is a need in the field of psychological health for a new and useful method for providing therapy to an individual. This invention creates such a new and useful method for providing therapy to an individual.

BRIEF DESCRIPTION OF THE FIGURES

FIGS. 10A-10D depict examples of population reports/tools provided to an entity in an embodiment of a method for providing therapy to an individual;

FIGS. 12A-12B depict examples of reports provided to entities associated with a method for providing therapy to an individual.

DESCRIPTION OF THE EMBODIMENTS

The following description of the embodiments of the invention is not intended to limit the invention to these embodiments, but rather to enable any person skilled in the art to make and use this invention.

1. Method

Figure 1A:
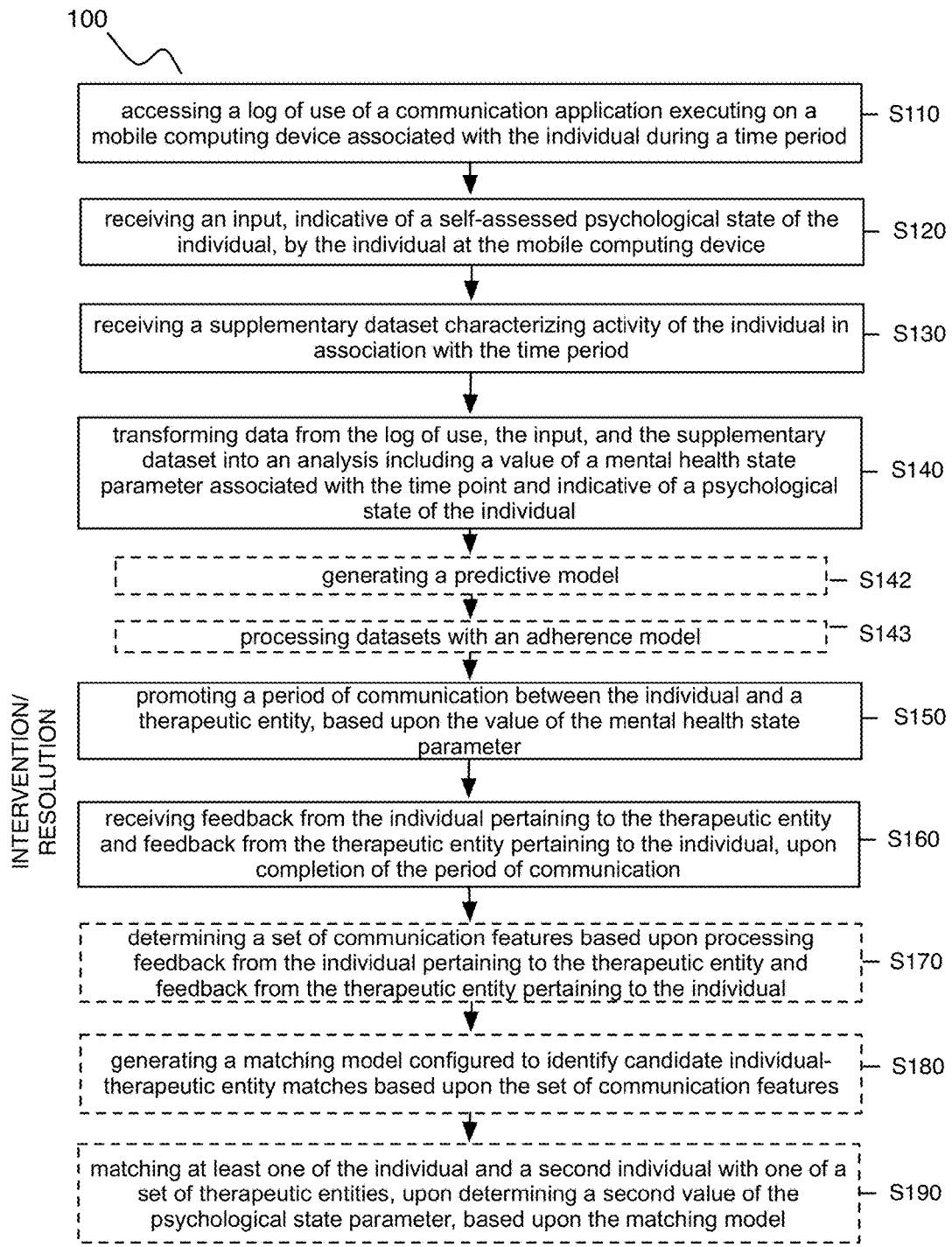
FIG. 1A is a flowchart of an embodiment of a method for providing therapy to an individual.

As shown in FIG. 1A, a method 100 for providing therapy to an individual includes: accessing a log of use of a communication application executing on a mobile computing device associated with the individual during a time period S110; receiving an input, indicative of a self-assessed psychological state of the individual, by the individual at the mobile computing device S120; receiving a supplementary dataset characterizing activity of the individual in association with the time period S130; transforming data from the log of use, the input, and the supplementary dataset into an analysis including a value of a mental health state parameter associated with the time point and indicative of a psychological state of the individual S140; promoting a period of communication between the individual and a therapeutic entity, based upon the value of the mental health state parameter S150; and receiving feedback from the individual pertaining to the therapeutic entity and feedback from the therapeutic entity pertaining to the individual, upon completion of the period of communication S160. In implementation of the method 100, the therapy preferably includes non-clinically-prescribed forms of therapy (e.g., therapeutic communication, health-related information, cognitive health-related tips, stress-relief therapy, measures to connect the individual with an entity who can provide any form of therapy). However, in alternative variations, the therapies covered can additionally or alternatively include clinical forms of therapy (e.g., supplements, medications, therapeutic substances, medical procedures, etc.), and any other suitable form of therapy.

In some variations, the method 100 can further include one or more of: determining a set of communication features based upon processing feedback from the individual pertaining to the therapeutic entity and feedback from the therapeutic entity pertaining to the individual S170; generating a matching model configured to identify candidate individual-therapeutic entity matches based upon the set of communication features S180; and matching at least one of the individual and a second individual with one of a set of therapeutic entities, upon determining a second value of the mental health state parameter, based upon the matching model S190.

The method 100 functions to analyze communication behavior and other information regarding an individual (e.g., a user, an individual affected by a life event) at risk of entering or experiencing a poor mental health state (e.g., depression state, stress state, anxiety state, etc.) that could adversely affect quality of life for the individual. As such, the method 100 can facilitate identification of mental health states of an individual and/or identification of trends in mental health states of the individual, while providing a therapeutic measure to the individual for improvement of the mental health state of the individual. In particular, the method 100 can be used to provide personalized therapy to an individual based upon their individual data, and to provide help to them in the moment or proximal in time to a time point at which they would benefit from a therapeutic measure. In a specific application, the method 100 can monitor and analyze communication behavior, mobility behavior, and/or other behavior detected from any other suitable sensor(s) associated with an individual who is not necessarily diagnosed with a disorder or condition, but who has experienced a recent disruptive life event.

The method 100 can additionally or alternatively be directed at any individual with mental health issues or emotional problems (diagnosed or undiagnosed). As such, the method 100 can connect the individual with an entity that provides the individual with an avenue for therapeutic communication or conversations. In connecting the individual with an entity, the individual can provide some input that initiates or prompts the connection, or the individual can otherwise be connected with the listening entity in any other suitable manner. Thus, the method 100 can provide a predictive model for one or more individuals who are at risk of entering or are experiencing an adverse mental health state, as well as an intervention model for providing therapeutic communication to the individual(s) at key time points at which communication would be beneficial to the individual(s). The intervention model can implement an anticipated adverse mental health state of an individual to automatically provide an avenue for the individual to receive therapeutic communication (e.g., via a phone call, text message, email, health tip notification, other electronic communication, other electronic device-based messaging, other electronic device-based notifications, etc.). Furthermore, in relation to the disclosure, the terms "entity", "listening entity", "listener", "coaching entity", "coach", "therapeutic entity" and "therapist" can refer to the same entity or different entities.

While the method 100 can be implemented for a single individual for whom therapeutic communication would be beneficial, the method 100 can additionally or alternatively be implemented for a population of individuals, wherein the population of individuals can include individuals similar to and/or dissimilar to the individual (e.g., in demographic group, in experience of a disruptive life event, etc.). Thus, information derived from the population of individuals can be used to provide additional insight into connections between the individual's behavior and risk of entering an adverse mental health state, due to aggregation of data from the population of individuals, which can be used to improve predictive models and/or build improved features into an application executing the method 100. In examples, the population of individuals can include individuals characterized or grouped by any suitable demographics, any type of issue for which individuals seek help, any type of behavior in interacting with the system(s) implementing the method 100, and any other suitable feature.

Furthermore, variations of the method 100 can include any particular subset of the described blocks, in providing help to an individual in a time of need. In one such variation, as shown in FIGS. 1C and 1D, one variation of the method 100 can include: at least one of Blocks S110 and S120 in receiving information pertaining to an induced state of stress of the individual S115'; allowing the individual to establish a period of communication between the individual and a therapeutic entity, based upon the information S150'; receiving feedback from the individual pertaining to the therapeutic entity and feedback from the therapeutic entity pertaining to the individual, upon completion of the period of communication S160'; and improving a subsequent period of communication, based upon the feedback received in Block S165'. This variation of the method 100 can allow an individual to contact a therapeutic entity to receive a period of therapeutic communication, with or without prompting derived from an extensive analysis of the individual's state.

The method 100 is preferably implemented at least in part by an embodiment of the system 200 described in Section 2 below; however, the method 100 can alternatively be implemented using any other suitable system configured to process communication and/or other behavior of the individual, in aggregation with other information, in order to provide therapeutic communication to individuals based upon analysis risk of entering adverse mental health states.

1.1 Method—Passive Data

Block S110 recites: accessing a log of use of a communication application (e.g., native communication application) executing on a mobile device by the individual within a time period, which functions to unobtrusively collect and/or retrieve communication-related data from an individual's mobile device. Preferably, Block S110 is implemented using a module of a processing subsystem configured to interface with a native data collection application executing on a mobile computing device (e.g., smartphone, tablet, personal data assistant (PDA), personal music player, vehicle, head-mounted wearable computing device, wrist-mounted wearable computing device, etc.) of the individual, in order to retrieve communication-related data pertaining to the individual. As such, in one variation, a native data collection application can be installed on the mobile computing device of the individual (e.g., upon election of installation by the individual, upon promotion of the application to the individual), can execute substantially continuously while the mobile computing device is in an active state (e.g., in use, in an on-state, in a sleep state, etc.), and can record communication parameters (e.g., communication times, durations, contact entities) of each inbound and/or outbound communication from the mobile computing device. In implementing Block S110, the mobile computing device can then upload this data to a database (e.g., remote server, cloud computing system, storage module), at a desired frequency (e.g., in near real-time, every hour, at the end of each day, etc.) to be accessed by the processing subsystem/computing system described in more detail below. In one example of Block S110, the native data collection application can launch on the individual's mobile device as a background process that gathers data once the individual logs into an account, wherein the data includes how and with what frequency the individual interacts with and communicates with other individuals through phone calls, e-mail, instant messaging, an online social network, and any other suitable form of communication, parameters of which can be electronically logged.

As such, in accessing the log of use of the communication application, Block S110 preferably enables collection of one or more of: phone call-related data (e.g., number of sent and/or received calls, call duration, call start and/or end time, location of individual before, during, and/or after a call, and number of and time points of missed or ignored calls); text messaging (e.g., SMS test messaging) data (e.g., number of messages sent and/or received, message length, message entry speed, delay between message completion time point and sending time point, message efficiency, message accuracy, time of sent and/or received messages, location of the individual when receiving and/or sending a message); data on textual messages sent through other communication venues (e.g., public and/or private textual messages sent to contacts of the individual through an online social networking system, reviews of products, services, or businesses through an online ranking and/or review service, status updates, "likes" of content provided through an online social networking system), vocal and textual content (e.g., text and/or voice data that can be used to derive features indicative of negative or positive sentiments) and any other suitable type of data.

Figure 1B:
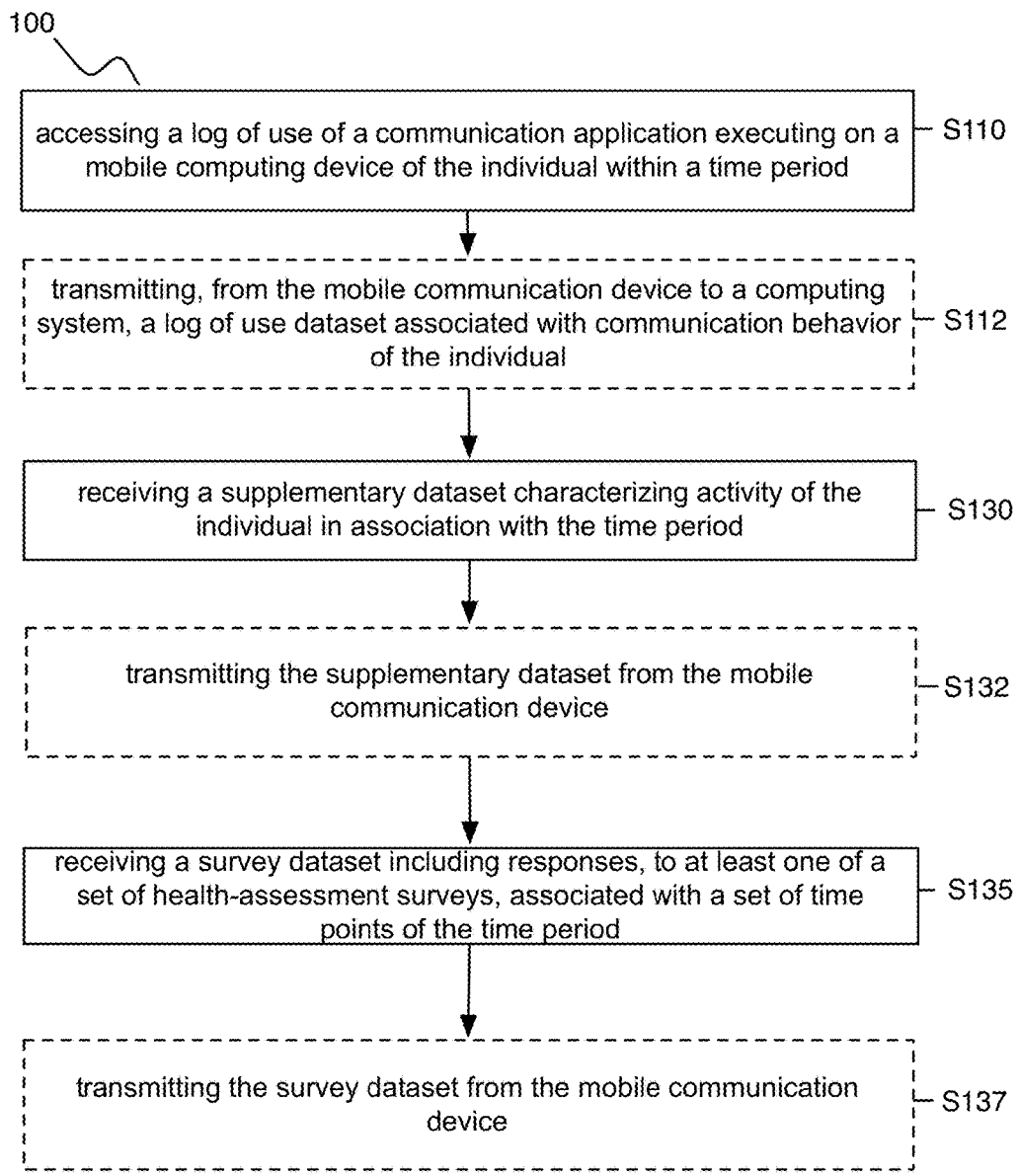
FIG. 1B is a flowchart of a portion of an embodiment of a method for providing therapy to an individual.
Figure 1C:
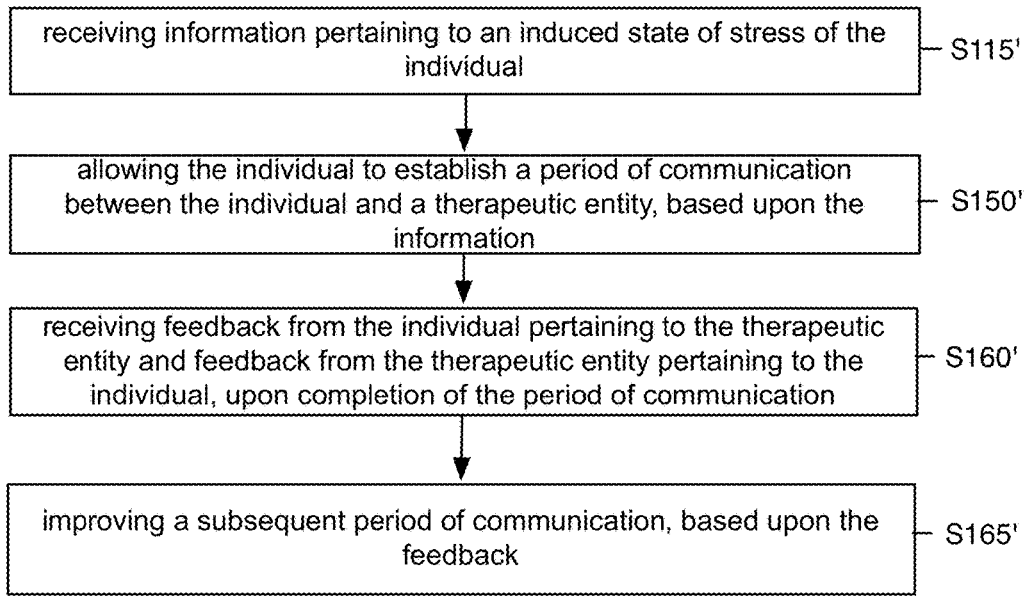
FIGS. 1C and 1D depict schematics of a variation of a method for providing therapy to an individual.
Figure 1D:
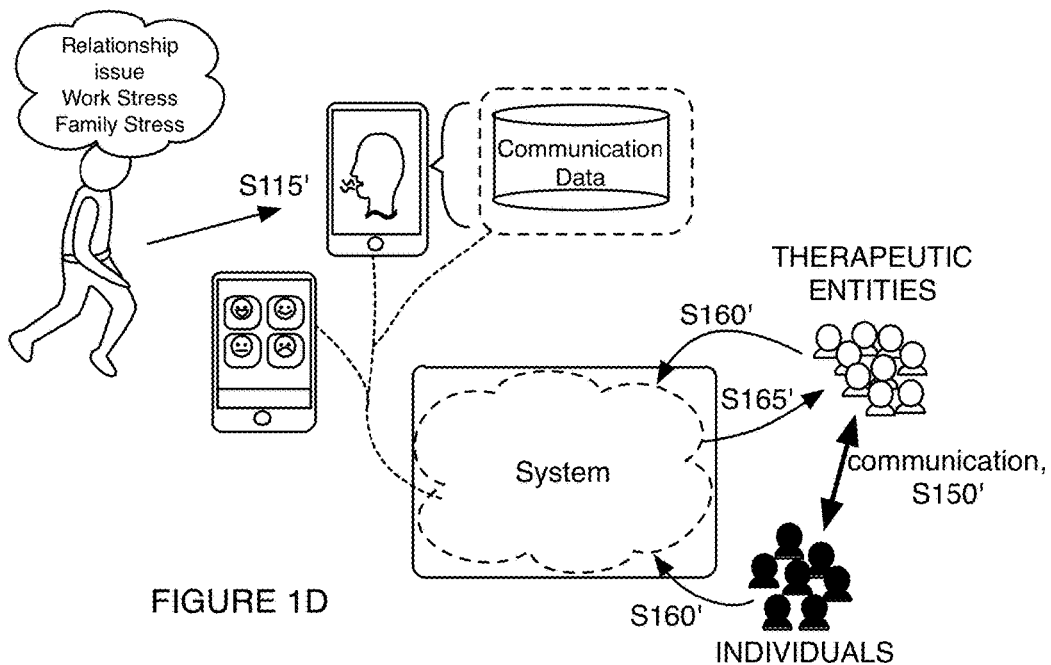

In relation to accessing the log of communication, Block S110 can include accessing the log of use at the mobile device of the individual, and transmitting, from the mobile device to a computing system, a log of use dataset associated with communication behavior of the individual S112, as shown in FIG. 1B. As such, Block S110 can comprise establishing communication between the computing system and a communication module of the mobile device of the individual, wherein the communication module comprises hardware elements that collect and/or aggregate data associated with communication behavior of the individual. The communication module can thus be accessed (with or without appropriate security aspects) by one or more other portions of the system implementing the method 100, in order to retrieve and process log of use data, according to additional Blocks of the method 100 (described in more detail below). The computing system can be implemented in one or more of a processing module of the mobile device, a personal computer, a remote server, a cloud-based computing system, a computing module of any other suitable computing device (e.g., mobile computing device, wearable computing device, etc.), and any other suitable computing module. In transmitting the log of use dataset, a communication module (e.g., a hardware communication module associated with the communication application) can transmit data to the computing system by way of a wired and/or wireless data link (e.g., a communicable link over Bluetooth, a communicable link over Bluetooth LTE, etc.). However, Block S110 can include another other suitable variation of accessing the log of communication, transmitting data from the log of communication, and/or receiving a log of use dataset.

Block S120 recites: receiving an input, indicative of a self-assessed mental health state of the individual, by the individual at the mobile computing device, which functions to provide an active data piece, provided by the individual, to supplement passive data obtained in other blocks of the method 100. The self-assessed mental health state of the individual can also function as a metric for purposes of comparison to a second self-assessed mental health state of the individual, after a period of communication with a therapeutic entity has been experienced (i.e., as in Block S150). Block S120 is preferably implemented at a module of the processing subsystem described in relation to Block S110 above, but can additionally or alternatively be implemented at any other suitable system configured to receive input data from one or more individuals interfacing with mobile devices.

Provision of the input in Block S120 is preferably prompted electronically from within an application executing at the mobile computing device of the individual; however, provision of the input can alternatively be self-elected without any prompting, or can alternatively be prompted in any other suitable manner (e.g., by email, by text message, by a mail service, by an in person interaction, etc.). Prompting for an input from the individual can occur with regular frequency (e.g., every morning, every night, once a week, etc.) or with irregular frequency. Prompting for an input from the individual can additionally or alternatively be prompted upon detection of behavior of the individual using sensors (e.g., of the mobile computing device, of any other device) associated with the individual. In one example, detection (e.g., using a GPS element) that the individual has entered or left a trigger location (e.g., a bar, a family member's home, etc.) can trigger prompting of input by the individual. In another example, detection of an elevated or depressed heart rate or breathing rate relative to baseline data (e.g., using a respiration sensor, using a heart rate sensor) can trigger prompting of input by the individual. Prompting for an input from the individual can additionally or alternatively be triggered by processing of passive data collected in other blocks of the method 100, such that a preliminary analysis of risk of entering an adverse mental health state triggers prompting of input provision. In one example, an analysis of one or more of: texting behavior (e.g., number of outgoing text messages, number of incoming text messages, frequency of text messaging, text message length, parties involved in a text message chain, etc.), calling behavior (e.g., number of outgoing calls, number of incoming calls, frequency of calling, call length, parties involved in a call), mobile computing device interaction behavior (e.g., screen unlocks, number of applications used, data usage by each of a set of applications, etc.), and any other passively collected data can be used to trigger prompting of provision of input by the individual. Additionally or alternatively, analysis of any of the above factors can be used to provide notifications and/or therapeutic measures (e.g., health tips, etc.) to the individual in any other suitable manner.

Figure 2:
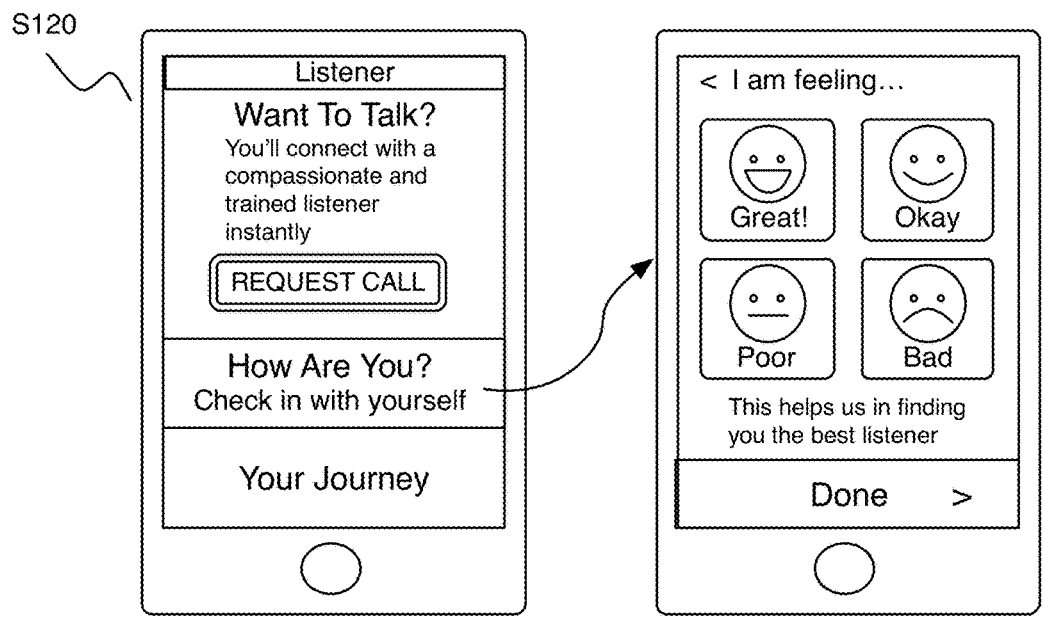
FIG. 2 depicts an example of providing an input according to an embodiment of a method for providing therapy to an individual.

Provision of the input can include selecting, at an input device (e.g., touch screen, voice command, keyboard, mouse, track pad, joystick, touch interface, etc.), one of a set of options describing candidate self-assessed mental health states (e.g., moods) of the individual. Provision of the input can additionally or alternatively include selecting one of a set of options describing recent life events (e.g., loss of a loved one, relationship issue, health issue, concern, etc.) of the individual. In one example, as shown in FIG. 2, the input can include a selection of one of a set of mental health states (e.g., feeling great, feeling okay, feeling poor, feeling bad), provided by an application executing at a mobile device of the individual, wherein selection is provided at a touch screen of the mobile device. The input can, however, include information not selected from a pre-selected list of options, and allow the individual to provide a customized input (e.g., a detailed description about how the individual is feeling). As such, the input can provide qualitative information and/or quantitative data, or qualitative information that can be transformed into quantitative data, for processing in subsequent Blocks of the method 100.

Figure 5A:
FIGS. 5A-5J depict an example of a method and system for providing therapy to an individual.
Figure 5B:
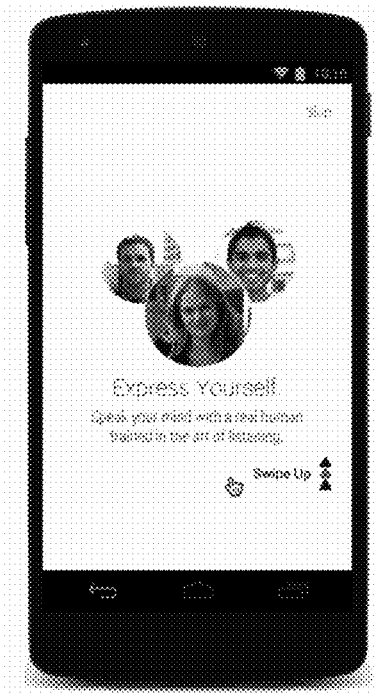
Figure 5C:
Figure 5D:
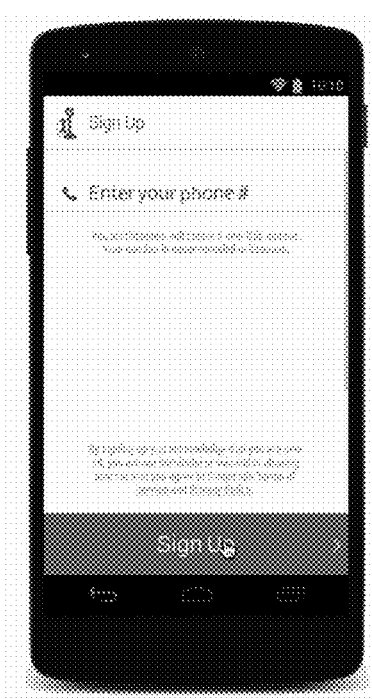
Figure 5E:
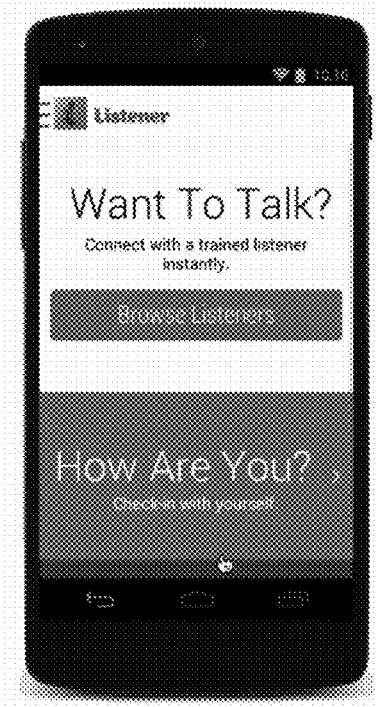
Figure 5F:

The input can additionally or alternatively include demographic information (e.g., gender information, ethnicity information, nationality information, socioeconomic status information, sexual orientation information, age information, etc.), behavioral information (e.g., substance use information, diet information, physical activity information, etc.), life event information (e.g., relationship information, positive event information, negative event information, etc.), contact information (e.g., phone number, email address, physical address, etc., as in FIG. 5D), individual-acquisition information (e.g., information regarding how the individual was exposed to the application/service), or other information that facilitates therapy provision and/or matching of the individual with a therapeutic entity in subsequent blocks of the method 100.

Block S130 recites: receiving a supplementary dataset characterizing activity of the individual in association with the time period, which functions to unobtrusively receive non-communication-related data from a patient's mobile communication device and/or other device configured to receive contextual data from the patient. Block S130 can include receiving non-communication-related data pertaining to the individual before, during, and/or after (or in the absence of) communication with another individual (e.g., a phone call) and/or computer network (e.g., a social networking application), as described above in relation to Block S110. Block S120 can include receiving one or more of: location information, movement information (e.g., related to physical isolation, related to lethargy), device usage information (e.g., screen usage information related to disturbed sleep, restlessness, and/or interest in mobile device activities), and any other suitable information. In variations, Block S120 can include receiving location information of the individual by way of one or more of: receiving a GPS location of the individual (e.g., from a GPS sensor within the mobile communication device of the individual), estimating the location of the individual through triangulation of local cellular towers in communication with the mobile communication device, identifying a geo-located local Wi-Fi hotspot during a phone call, and in any other suitable manner. In applications, data received in Block S110 and S130 can be processed to track behavior characteristics of the individual, such as mobility, periods of isolation, quality of life (e.g., work-life balance based on time spent at specific locations), periods of disrupted sleep, and any other location-derived behavior information.

As such, data from Blocks S110 and S130 can be merged (e.g., features extracted from outputs of Blocks S110 and S130 can be co-processed or otherwise combined) in subsequent blocks of the method 100 to track the individual's mobility during a communication, for instance, in the analysis of Block S140. In variations, Block S130 can additionally or alternatively include receiving mobile usage data, including data indicative of screen unlocks and mobile application usage (e.g., by retrieving usage information from mobile operating system logs, by retrieving usage information from a task manager on a mobile communication device, etc.). Blocks S120 and/or S110 can therefore facilitate tracking of variations and periods of activity/inactivity for a patient through automatically collected data (e.g., from the patient's mobile communication device), in order to enable identification of periods of activity and inactivity by the individual (e.g., extended periods when the individual was hyperactive on the device or not asleep).

In additional variations, Block S130 can additionally or alternatively include receiving one or more of: physical activity- or physical action-related data (e.g., accelerometer data, gyroscope data, data from an M7 or M8 chip) of the individual, local environmental data (e.g., climate data, temperature data, light parameter data, etc.), nutrition or diet-related data (e.g., data from food establishment check-ins, data from spectrophotometric analysis, etc.) of the individual, biometric data (e.g., data recorded through sensors within the individual's mobile device, data recorded through a wearable or other peripheral device in communication with the individual's mobile device) of the individual, and any other suitable data. In more detail, variations of biometric signals that can contribute to features (e.g., features indicative of pain/reduced function) processed/analyzed according to blocks of the method 100 can include any one or more of: electromyograph (EMG) signals, electrocardiography (ECG) signals, electroencephalograph (EEG) signals, galvanic skin response (GSR) signals, bioelectrical impedance (BIA) signals, any other suitable bioelectrical signal of the individual, respiration signals, body temperature, and any other suitable biometric information of the individual. Furthermore, environmental sensors (e.g., temperature sensors, air-quality sensors, ambient light sensors, etc.) can provide contextual information from the environment of the individual to provide additional supplemental data. In examples, one or more of an accelerometer (e.g., multi-axis accelerometer) and a gyroscope (e.g., multi-axis gyroscope) of a mobile computing device of the patient can be configured to enable detection of changes in gait of a patient exhibiting osteoarthritis symptoms, and to transmit data to a processing subsystem implementing portions of the method 100; thus, Block S130 can include receiving this data to further augment analyses performed in Block S140.

In variations, Block S130 can include receiving location information of the individual by way of one or more of: receiving a GPS location of the individual (e.g., from a GPS sensor on-board the mobile computing device of the individual), estimating the location of the individual through triangulation of local cellular towers in communication with the mobile computing device, identifying a geo-located local Wi-Fi hotspot during a phone call, and any other suitable method for location approximation/identification. In applications, data received in Block S110 and S130 can be processed to track behaviors of the individual, such as behaviors indicative of mobility, behaviors indicative of periods of isolation, behaviors indicative of quality of life (e.g., work-life balance based on time spent at specific locations), and any other location-derived behavior information. As such, data from Blocks S110 and S130 can be merged to track the individual's mobility during a communication, in the analysis of Block S140. In variations, Block S130 can additionally or alternatively include receiving mobile device usage data, including data indicative of screen unlocks and mobile application usage (e.g., by retrieving usage information from mobile operating system logs, by retrieving usage information from a task manager on a mobile computing device, etc.). Blocks S130 and/or S110 can therefore facilitate tracking of variations and periods of activity/inactivity for an individual through automatically collected data (e.g., from the individual's mobile computing device), in order to enable identification of periods of activity and inactivity of the individual (e.g., periods when the individual was hyperactive on the device or not asleep).

In relation to receiving data, Blocks S130 and/or S110 can additionally or alternatively include receiving data pertaining to individuals in contact with the individual during the period of time, such that data from the individual and data from one or more individuals in communication with the individual are received (e.g., using information from an analogous application executing on the electronic device(s) of the individual(s) in communication with the individual). As such, Blocks S130 and/or S110 can provide a holistic view that aggregates communication behavior data and contextual data of two sides of a communication involving the individual. In examples, such data can include one or more of: an associated individual's location during a phone call with the individual, the associated individual's phone number, the associated individual's length of acquaintance with the individual, and the associated individual's relationship to the individual (e.g., top contact, spouse, family member, friend, coworker, business associate, etc.).

Similar to Block S110, in relation to receiving the supplementary dataset, Block S130 can include transmitting the supplementary dataset from the mobile communication device S132 and/or any other suitable device (e.g., wearable device, biometric monitoring device, etc.) or system that serves as a source of supplementary data, to the computing system, as shown in FIG. 1B. In transmitting the supplementary dataset, one or more sensor modules (e.g., sensor module of the mobile communication device, sensor module of a wearable computing device, sensor of a biometric monitoring device, etc.) can transmit data to the computing system by way of a wired and/or wireless data link (e.g., over Bluetooth, over Bluetooth LTE, etc.). As such, establishing of a communicable link (e.g., automatically, in response to a triggering condition, manually, etc.) can facilitate transmission of desired data in Block S130. However, Block S130 can include any other suitable variation of transmitting supplementary data, and/or receiving supplementary data.

1.2 Method—Active Data

In some variations, the method can additionally or alternatively include Block S135, which recites: receiving a survey dataset including responses, to at least one of a set of health-assessment surveys, associated with a set of time points of the time period, from the individual. Block S135 is preferably implemented at a module of the computing system described in relation to Blocks S110-S130 above, but can additionally or alternatively be implemented at any other suitable system configured to receive survey data from one or more individuals. The survey dataset can include interview and/or self-reported information from the individual. Furthermore, the survey dataset preferably includes quantitative data, but can additionally or alternatively include qualitative data pertaining to a mental health state of the individual corresponding to at least a subset of the set of time points. Furthermore, while portions of the survey dataset preferably correspond to time points within the time period of Block S110, portions of the survey dataset can alternatively correspond to time points outside of the time period of Block S110 (e.g., as in a pre-screening or a post-screening survey). Additionally or alternatively, Block S130 can include receiving clinical data (e.g., information gathered in a clinic or laboratory setting by a clinician).

In Block S135, the set of time points can include uniformly or non-uniformly-spaced time points, and can be constrained within or extend beyond the time period of the log of use of the communication application of Block S110. As such, in variations, the set of time points can include regularly-spaced time points (e.g., time points spaced apart by an hour, by a day, by a week, by a month, etc.) with a suitable resolution for enabling detection of changes in a mental health state of the individual. Additionally or alternatively, provision of a survey and/or reception of responses to a survey can be triggered upon detection of an event of the individual (e.g., based upon data from sensors associated with the individual, based upon an output of an analysis of Block S140, etc.) or any other suitable change in state of the individual. Furthermore, for all time points of the set of time points, an identical subset of the set of health-assessment surveys can be provided to the individual; however, in alternative variations, different subsets of the set of health-assessment surveys can be provided to the individual at different time points of the set of time points.

In variations, the survey dataset can include responses to surveys configured to assess severity of mental health state in an individual along a spectrum, wherein the surveys transform qualitative information capturing an individual's affective state into quantitative data according to a response-scoring algorithm. In examples, the set of health-assessment surveys can include surveys derived from one or more of: the Hamilton Rating Scale for Depression (HAM-D), with scores scaling from 0 (least severe) to 58 (most severe); the Patient Health Questionnaire (PHQ-9, PHQ-2) for screening, monitoring, and measuring depression severity according to Diagnostic and Statistical Manual (DSM) criteria for depression, with scores scaling from 0 (least severe) to 27 (most severe); the World Health Organization (WHO-5) quality of life assessment, with scores scaling from 0 (most severe) to 25 (least severe); the Patient Activation Measure (PAM) self-management assessment with levels scaling from 1 (most severe) to 4 (least severe); a demographic survey that receives demographic information of the patient; a medication adherence survey (for patients taking medication for depression); a mood/depression survey; and a recent care survey (e.g., covering questions regarding hospitalization and psychological care). However, the set of surveys can include any other suitable surveys (e.g., BDI, HDI, CES-D, PHQ-8, etc.) or adaptations thereof. As such, the survey dataset can include quantitative scores of the individual for one or more subsets of surveys for each of the set of time points (or a subset of the set of time points).

In relation to anxiety, which may or may not be comorbid with a mental health state of the individual, the survey dataset can include responses to surveys configured to assess severity of anxiety in an individual along a spectrum, wherein the surveys transform qualitative information capturing an individual's state into quantitative data according to a response-scoring algorithm. In examples, surveys configured to assess states of anxiety can include surveys derived from one or more of: a general anxiety disorder (GAD) scale (e.g., a GAD-7 scale); a questionnaire for screening, monitoring, and measuring anxiety severity according to Diagnostic and Statistical Manual (DSM) criteria for anxiety; a daily assessment of symptoms—anxiety (DAS-A) questionnaire; a questionnaire for screening, monitoring, and measuring compulsive behavior severity according to Diagnostic and Statistical Manual (DSM) criteria for compulsive behavior; a Yale-Brown Obsessive Compulsive Scale (Y-BOCS); a questionnaire for screening, monitoring, and measuring panic attack severity according to Diagnostic and Statistical Manual (DSM) criteria for anticipatory attacks (DSM-IV-TR); a questionnaire for screening, monitoring, and measuring PTSD according to Diagnostic and Statistical Manual (DSM) criteria for PTSD; a Trauma Screening Questionnaire; a PTSD symptom scale; a social phobia inventory; a SPAI-B tool; a Liebowitz Social Anxiety Scale; a questionnaire for screening, monitoring, and measuring specific phobia severity according to Diagnostic and Statistical Manual (DSM) criteria for specific phobias (DSM-IV-TR); and any other suitable tool or survey.

In an example, the survey dataset comprises biweekly responses (e.g., for a period of 6 months) to the PHQ-9 survey, biweekly responses (e.g., for a period of 6 months) to the WHO-5 survey in alternation with the PHQ-9 survey, responses to the PAM assessment at an initial time point, at an intermediate time point (e.g., 1-month time point), and at a termination time point, responses to the HAM-D assessment at an initial time point and a termination time point, biweekly response to a recent care survey, daily responses to a mood survey, and twice-per-week responses to a medication adherence survey.

In some variations, Block S135 can further include facilitating automatic provision of at least one of the set of health-assessment surveys at the mobile communication device(s) of the individual(s). As such, responses to one or more of the set of health-assessment surveys can be provided by user input at an electronic device (e.g., a mobile communication device of the patient), or automatically detected from user activity (e.g., using suitable sensors). Additionally or alternatively, provision of at least one of the set of health-assessment surveys can be performed manually by an entity (e.g., therapy providing entity, healthcare professional, relative, acquaintance, etc.) associated with an individual or received as derived from clinical data, with data generated from the survey(s) received in Block S130 by manual input. Additionally or alternatively, provision of at least one survey and/or reception of responses to the survey can be guided by way of an application executing at a device (e.g., mobile device, tablet) of a caretaker of the individual and/or the patient, wherein the application provides instruction (e.g., in an audio format, in a graphic format, in a text-based format, etc.) for providing the survey or the responses to the survey. Block S130 can, however, be implemented in any other suitable manner (e.g., by verbal communication over the phone, by verbal communication face-to-face, etc.).

Similar to Block S110, In relation to receiving the survey dataset, Block S135 can include transmitting the survey dataset from the mobile communication device S137 and/or any other suitable device or system that serves as a source of survey data, to the computing system, as shown in FIG. 1B. In transmitting the survey dataset, one or more data storage modules (e.g., memory module of the mobile communication device, etc.) can transmit data to the computing system by way of a wired and/or wireless data link (e.g., over Bluetooth, over Bluetooth LTE, etc.). However, Block S130 can include another other suitable variation of transmitting survey data, and/or receiving survey data.

Blocks S110, S120, S130, and S135 can thus provide passive data (e.g., unobtrusively collected data) and active data (e.g., survey data) that can be taken as inputs in Block S140 to generate analyses pertaining to present, past, and/or future mental health states of a patient.

1.3 Method—Modeling and Predicting Health State

Block S140 recites: transforming data from the log of use, the input, and the supplementary dataset into an analysis including a value of a mental health state parameter associated with the time point and indicative of a mental health state of the individual. Block S140 functions to determine a value of a mental health state parameter in association with a time point of the time period, as an output of a risk model that assesses the individual's current state of wellbeing, in identifying when the individual may be in need of therapeutic communication, and/or predicts risk that the individual will trend toward an adverse state (e.g., mental state unrelated to a diagnosable condition, stress state, depression state, anxiety state) without any intervention. As such, Block S140 can, in some specific applications, be used to enable identification of aberrant patterns and/or predict when the individual could benefit from therapeutic communication with a listening entity, relation to one or more of stress (e.g., work-induced stress), relationship issues (e.g., an argument with a significant other, issues with family members, etc.), and any other state. Preferably, the analysis includes utilization of one or more machine learning techniques and training data (e.g., from the individual, from a population of individuals), data mining, and/or statistical approaches to generate more accurate models pertaining mental health states of wellbeing for the individual and/or a wider population of individuals associated with the method 100, as described in more detail below. As such, Block S140 is preferably implemented at a processing subsystem (e.g., the processing subsystem associated with Blocks S110-S130) configured to process data from the log of use, inputs by the individual, and the supplementary dataset; however, the analysis of Block S140 can alternatively be implemented in any other suitable manner. Furthermore, outputs of the analysis can be used to tailor promotion of communication in a manner correlated with severity of the individual's state (e.g., an extent of need for therapeutic communication). In variations, the analysis can provide lower precision in detection of a time point at which the individual is experiencing a non-critical state of being, and the analysis can be used to facilitate minimally-intrusive promotion of communication between the individual and a therapeutic entity (which the individual can respond to or ignore).

In the analysis, Block S140 can identify parameters/triggering events directly from passive data (i.e., the log of use dataset, the supplementary dataset) and/or from active data (i.e., the input, the survey dataset), or can additionally or alternatively implement a predictive model that processes both passive and active components to predict one or more present or future states of the individual, with training data.

Additionally or alternatively, for individuals following a medication regimen for treatment or maintenance of health in relation to a health state, the analyses of Block S140 can include generation of an adherence model that assesses or predicts adherence of the patient to the medication regimen as an output of the analysis.

1.3.1 Mental Health State—Predictive Model

Preferably, generating a predictive model S142 in association with Block S140 includes utilization of one or more machine learning techniques and training data (e.g., from the patient, from a population of patients), data mining, and/or statistical approaches to generate more accurate models pertaining to the patient's mental health (e.g., over time, with aggregation of more data). As such, Block S142 is preferably implemented at a computing system configured to process data from the log of use dataset, the supplementary dataset, and the survey dataset. The computing system can be the same computing system associated with one or more of Blocks S110-S130 of the method 100, or can alternatively be any other suitable computing system.

In generating the predictive model, Block S142 preferably uses input data including communication behavior data from the log of use, data from the supplementary dataset, data from the input, and additionally or alternatively, data from the survey dataset to provide a set of feature vectors corresponding to time points of the time period. Feature selection approaches can include one or more of: factor analysis approaches that implement statistical methods to describe variability among observed features in terms of unobserved factors, in order to determine which features explain a high percentage of variation in data; correlation feature selection (CFS) methods, consistency methods, relief methods, information gain methods, symmetrical uncertainty methods, and any other suitable methods of feature selection. In variations, feature selection approaches can be implemented for any passive data (e.g., communication data, mobility data), wherein a linking analysis of Block S140 is then used to determine associations between features of passive data and states of disorder determined from active data (e.g., survey response datasets). Analysis of the passive data in relation to the active data, with regard to feature selection and associations between passive and active data can, however, be performed in any other suitable manner.

In one variation, the feature vectors can include features related to aggregate communication behavior, interaction diversity, mobility behavior (e.g., mobility radius as a measure of distance traveled by the individual within a given time period, such as the weekend), a number of missed calls, and a duration of time spent in a certain location (e.g., at home). In examples, feature vectors can be generated based upon aggregation of phone, text message, email, social networking, and/or other patient communication data for a particular period of time into one or more features for the patient for the particular time period. Furthermore, a feature can be specific to a day, a week, a month, a day period (e.g., morning, afternoon, evening, night), a time block during a day (e.g., one hour), a specific communication action (e.g., a single phone call, a set of communication actions of the same type (e.g., a set of phone calls within a two-hour period), all communications within a period of time, etc.). Additionally, combinations of features can be used in a feature vector. For example, one feature can include a weighted composite of the frequency, duration (i.e., length), timing (i.e., start and/or termination), and contact diversity of all outgoing voice (e.g., phone call) communications and a frequency, length, and timing and/or response time to (i.e., time to accept) incoming voice communications within the first period of time through a phone call application executing on the patient's mobile computing device. Feature vectors can additionally or alternatively include features based on analysis of voice communications, textual communications, mobile application activity usage, location data, and any other suitable data which can be based on variance, entropy, or other mathematical and probabilistic computations of basic data (e.g., a composite activity score, a composite socialization score, a work-life balance score, a quality-of-life score). However, the feature vectors can be determined in any other suitable manner.

In some variations, Block S142 can include utilizing statistics-based feature selection approaches to determine a subset of features from the log of use dataset, the supplementary dataset, and/or the survey dataset that have a high predictive power and/or high accuracy in generating one or more outputs of the predictive model. In examples, the statistical approaches can implement one or more of: correlation-based feature selection (CFS), minimum redundancy maximum relevance (mRMR), Relief-F, symmetrical uncertainty, information gain, decision tree analysis (alternating decision tree analysis, best-first decision tree analysis, decision stump tree analysis, functional tree analysis, C4.5 decision tree analysis, repeated incremental pruning analysis, logistic alternating decision tree analysis, logistic model tree analysis, nearest neighbor generalized exemplar analysis, association analysis, divide-and-conquer analysis, random tree analysis, decision-regression tree analysis with reduced error pruning, ripple down rule analysis, classification and regression tree analysis) to reduce questions from provided surveys to a subset of effective questions, and other statistical methods and statistic fitting techniques to select a subset of features having high efficacy from the data collected in Blocks S110, S120, and/or S130. Additionally or alternatively, any assessment of redundancy or efficacy in a feature derived from data of Blocks S110, S120, and/or S130 can be used to provide a measure of confidence in an output of the predictive model from one or more input features. Furthermore, the statistical approach(es) of Block S142 can be used to strategically reduce portions of data collected based upon redundancy and/or lack of utility of the data. Even further, the statistical approaches/feature selection approaches can be used to entirely omit collection of portions of the data (e.g., responses to specific surveys or portions of surveys can render responses to other portions of surveys or other surveys redundant), in order to streamline the data collection in Blocks S110, S120, and/or S130.

In one example, a high degree of correlation (e.g., positive correlation) between responses to a bi-weekly PHQ-9 assessment and a daily mood survey (e.g., a portion of recent responses to a daily mood survey in relation to a time point of interest, responses to the daily mood survey from 7 days before and 7 days after a session of responses to a PHQ-9 assessment) can be used to entirely omit provision of the bi-weekly PHQ-9 assessment or portions of the PHQ-9 assessment, in lieu of the daily mood survey, due to redundancy in data collection, in variations of the method 100. In another example, a high degree of correlation (e.g., positive correlation) between responses to a bi-weekly PHQ-9 assessment and mobility data from the supplementary dataset can be used to entirely omit provision of the bi-weekly PHQ-9 assessment or portions of the PHQ-9 assessment, in lieu of the mobility data, due to redundancy in data collection, in variations of the method 100. In still another example, a high degree of correlation (e.g., positive correlation) between a communication parameter derived from the log of use (e.g., call count predictability) and mobility data from the supplementary dataset can be used to entirely omit collection of data (e.g., call count data, mobility data) due to redundancy in data collection, in variations of the method 100. In still another example, a high degree of correlation (e.g., positive correlation) between a communication parameter derived from the log of use (e.g., predictability and entropy) and mobility data from the supplementary dataset can be used to entirely omit collection of data (e.g., call count data, mobility data) due to redundancy in data collection, in variations of the method 100.

In still other examples, correlations between active data and passive data including one or more of: positive correlations between daily mood survey score and call count/SMS count during peak hours, positive correlations between daily mood survey score and communication diversity, negative correlations between daily mood survey score and incoming call count during off-peak hours, negative correlations between daily mood survey score and SMS message length to a primary contact during peak hours, negative correlations between daily mood survey score and number of unreturned calls during off-peak hours, positive correlations between PHQ-9 assessment score and mobility, positive correlations between PHQ-9 assessment score and mobility radius, and negative correlations between PHQ-9 assessment score and call count predictability can be used to streamline data collection associated with Blocks S110, S120, and/or S130. However, any other suitable data derived from Blocks S110, S120, and S130 can be used to increase efficacy of data collection and/or determination of values of the mental health state parameter in Block S142. Additionally or alternatively, any assessment of redundancy or efficacy in a feature derived from data of Blocks S110, S120, and/or S130 can be used to provide a measure of confidence in outputs of the predictive model determined from the feature(s).

In some embodiments, the predictive model generated in Block S142 can process a set of feature vectors according to methods described in relation to the predictive modeling engine described in U.S. application Ser. No. 13/969,339, entitled "Method for Modeling Behavior and Health Changes" and filed on 16 Aug. 2014, which is incorporated herein in its entirety by this reference; however, the predictive model can alternatively be generated in any other suitable manner. As such, in variations of the model(s), a set of feature vectors from the input data can be processed according to a machine learning technique (e.g., support vector machine with a training dataset) to generate the value(s) of the criticality parameter in association with a time point. In one example, the predictive model can incorporate historical data from the patient (e.g., survey responses from a prior week, a history of passive data from the log of use, etc.), with more weight placed upon more recent data from Blocks S110-S130 in determination of a mental health state associated with a time point by the predictive model; however, the predictive model can be implemented in any other suitable manner.

Furthermore, in extensions of the method 100 to a population of patients, the predictive model can be used to identify differences in passive data and/or active data, as associated with identified mental health states, between different demographics of individuals. For instance, the predictive model can be used to identify sets of feature vectors and/or subsets of features (e.g., related to communication behavior, related to survey responses, related to mobility behavior, etc.) that have high efficacy in determining risk/severity for one or more of: different genders, different age groups, different employment statuses, different ethnicities, different nationalities, different socioeconomic classes, and any other suitable demographic difference.

While some variations of machine learning techniques are described above, in relation to generation of the predictive model, Block S140 can additionally or alternatively utilize any other suitable machine learning algorithms. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

1.3.2 Health State—Adherence Model

For patients taking medication to manage their mental health state (or other health state), Block S140 can additionally or alternatively include processing datasets associated with Blocks S110, S120, and/or S130 with an adherence model S143 configured to assess and/or predict a state of adherence to a medication regimen by a patient. The adherence model can be an embodiment, variation, or example of an adherence model as described in U.S. application Ser. No. 13/969,339, entitled "Method for Modeling Behavior and Health Changes", but can alternatively be any other suitable adherence model.

1.3.3 Health State—Parameters of Analysis and Criticality Assessment

Figure 1E:
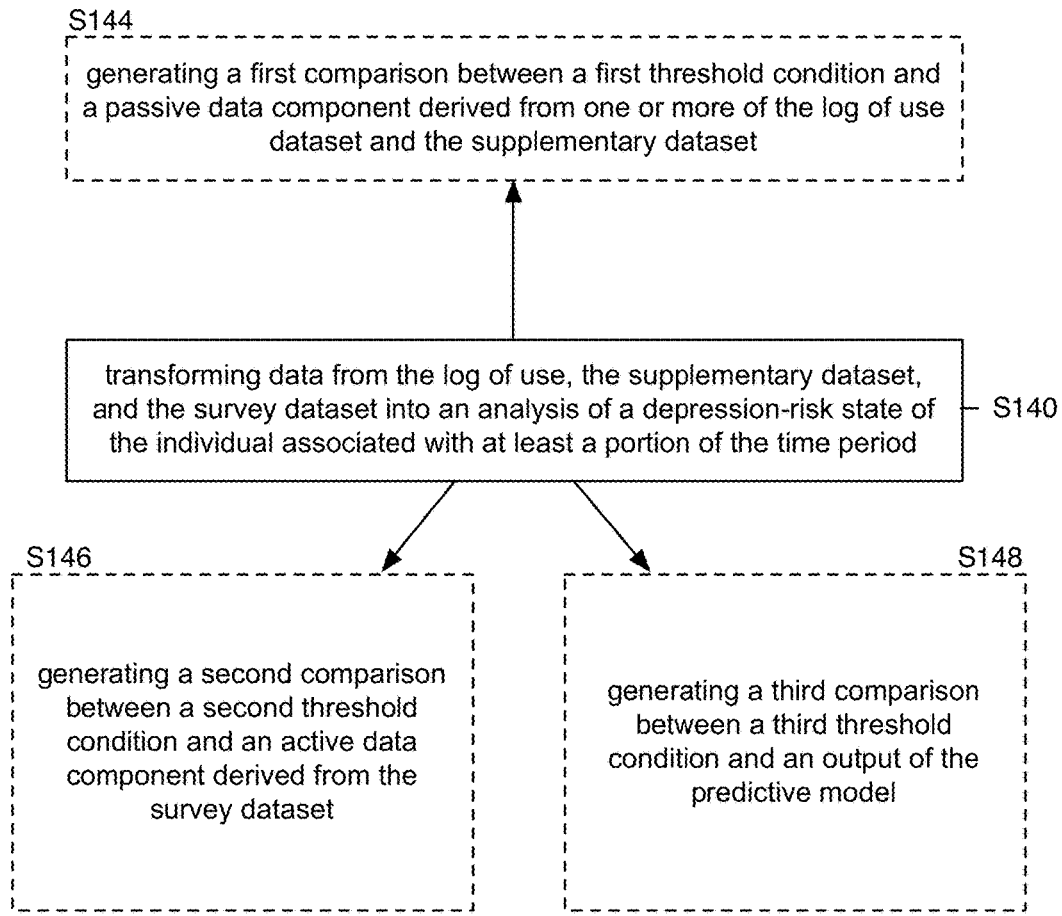
FIG. 1E is a flowchart of a portion of an embodiment of a method for providing therapy to an individual.

In generating the analysis of a mental health state of the individual, Block S140 can include generating comparisons between different threshold conditions and one or more of: components of the log of use dataset, components of the supplementary dataset, components of the survey dataset and outputs of the predictive model. As such, generating the analysis of the mental health state of the individual in Block S140 can include one or more of: generating a first comparison between a first threshold condition and a passive data component derived from one or more of the log of use dataset and the supplementary dataset S144; generating a second comparison between a second threshold condition and an active data component derived from the survey dataset S146; and generating a third comparison between a third threshold condition and an output of the predictive model S148, as shown in FIG. 1E. The comparisons of Blocks S144, S146, and/or S148 can thus be associated with parameters of the mental health state of the individual used to assess criticality of the mental health state of the individual, and/or to resolve a critical mental health state of the individual in subsequent blocks of the method 100.

Blocks S144, S146, and S148 can be implemented in a manner similar to that described in U.S. application Ser. No. 14/839,053, entitled "Method for Modeling Behavior and Depression State" and filed on 28 Aug. 2015, U.S. application Ser. No. 14/839,232, entitled "Method for Modeling Behavior and Psychotic Disorders" and filed on 28 Aug. 2015, and U.S. application Ser. No. 14/934,893, entitled "Method for Managing Patient Quality of Life" and filed on 6 Nov. 2015, which are each incorporated in its entirety by this reference.

1.4 Method—Therapeutic Listening Entity

Block S150 recites: promoting a period of communication between the individual and a therapeutic entity, based upon the value of the mental health state parameter, which functions to provide the individual with an avenue for receiving therapeutic communication with empathetic listening, intended to improve the individual's mental health state (e.g., in the short term, in the short term and long term, in the long term, etc.). Block S150 preferably includes providing the individual with an option to establish communication with a therapeutic entity, wherein conversing with the therapeutic entity serves as a form of therapy to improve the psychological state of the individual. Similar to above blocks of the method 100, Block S150 can further include: in response to at least one of: election of the option by the individual, an analysis of the passive dataset and the input/survey dataset, and an output of the predictive model, enabling a communicable link between the mobile device and a therapeutic entity communication device. Block S150 can then further include: by way of the communicable link, establishing a period of communication between the individual and the therapeutic entity, thereby providing therapy to the individual. In Block S150, promotion of the period of communication is preferably performed in a minimally- or non-intrusive manner, such that the individual is not perturbed or disincentivized from using with a system implementing the method 100. As such, promotion of the period of communication can be performed in a manner that is easily dismissed (e.g., with a "swipe-to-ignore" action by the user, in a manner that does not include reminders, etc.).

In one variation of Block S150, a portion of the application executing on the mobile computing device of the individual can prompt the individual to communicate with one of a set of therapeutic entities, as indicated by an output of the analysis, giving the individual the option to open communication with the therapeutic entity. Upon election by the individual to begin communication with the therapeutic entity, the application can then interface with calling functions of the mobile computing device to enable initiation of calling of the therapeutic entity selected by the individual. In alternative variations, the therapeutic entity can be automatically matched to the individual based upon a matching module (e.g., as described in relation to Blocks S180 and S190 below), upon election of opening communication by the individual. In still alternative variations, a therapeutic entity (e.g., matched to the individual, unmatched to the individual) can be automatically connected to the individual for a period of communication without election by the individual, based upon the analysis of Block S140. In still alternative variations, the individual can initiate the period of communication without any prompting. In still alternative variations, any other non-calling form of communication can be promoted and/or established between the individual and the therapeutic entity.

The therapeutic entity of Block S150 is preferably one of a set of therapeutic entities available (or potentially available) to communicate with the individual. Furthermore the therapeutic entity is preferably someone that is a stranger (e.g., an entity that is unknown to the individual, an entity whose identity is concealed from the individual), such that the individual can avoid any aversion of sharing sensitive information with a known entity. In an example, as shown in FIGS. 3A-3E, the therapeutic entity is an anonymous entity, the period of communication is held in confidentiality and neither party in the communication knows each other. Furthermore, in the example, the individual is encouraged to be genuine and open-minded in communicating with the therapeutic entity. However, the therapeutic entity can alternatively be someone who is not a stranger to the individual, and the set of therapeutic entities can include one or more entities that the individual is acquainted with. In variations, the set of therapeutic entities includes entities who have undergone training (e.g., by an overseeing entity associated with the method 100 and/or system), such that the therapeutic entities are sufficiently capable of improving an adverse psychological state of the individual; however, the set of entities can alternatively include one or more untrained entities. In specific examples, the set of therapeutic entities can include entities who have undergone identical training in handling a range of topics (e.g., relationship issues, loss issues, substance abuse issues, anxiety issues, stress issues, etc.). Additionally or alternatively, the set of therapeutic entities can include one or more specialized entities, each specializing in a specific topic (e.g., trained in handling one or more of: relationship issues, loss issues, substance abuse issues, anxiety issues, stress issues, etc.). Additionally or alternatively, a therapeutic entity can be provided with historical data pertaining to an individual who selects them (e.g., if the individuals have a history of communication with therapeutic entities associated with the method 100), in order to prepare the therapeutic entity for communication with the individual. In promoting the period of communication, information pertaining to the therapeutic entity(ies), including one or more of: type of training, gender, appearance, age, expertise, experience, rating (e.g., based upon historical periods of communication), and any other suitable information can be shared with the individual. In relation to the above, in repeat periods of communication promoted in repeat instances of Block S150, the individual can be connected with the same therapeutic entity across all instances of communication, or can alternatively be connected with different therapeutic entities across different instances of communication. Furthermore, variations of Block S150 can include enabling communication with parties comprising multiple individuals and/or multiple therapeutic entities (e.g., in a group therapy session format).

Preferably, the period of communication is subject to a financial cost that the individual is accountable for. In variations, the financial cost can be billed to the individual according to a cost model including one or more of: a time-based rate (e.g., a per-minute rate, an hourly rate), a discounted rate (e.g., for multiple periods of communication), a membership rate (e.g., a monthly membership that covers an unlimited number of periods of communication), a supply-based rate (e.g., surge pricing and/or discounted pricing depending upon the number of therapeutic entities available for communication), a fixed rate for each period of communication, and any other suitable pricing model. In some variations, selection of a maximum cost for the period of communication can enable automatic termination of the communication once the maximum cost has been reached (e.g., based upon a time-based rate of communication). The cost model preferably includes provisions that facilitate queue management for a therapeutic entity and/or supply of therapeutic entities available for communication. However, in some variations, the period of communication can alternatively have no associated financial cost that the individual is accountable for, and queue management/therapeutic entity supply can be handled in any other suitable manner.

Figure 4A:
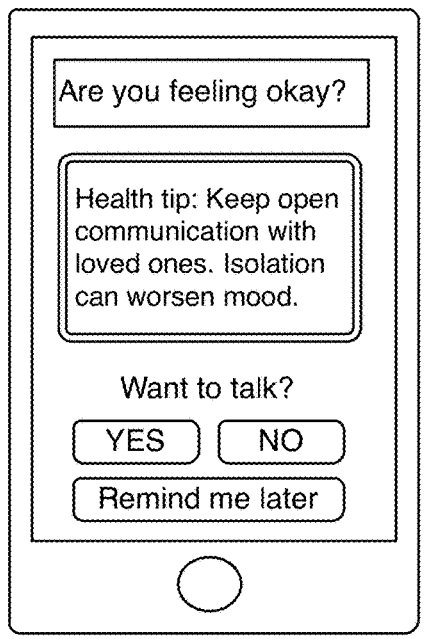
FIGS. 4A-4B depict examples of therapy provision in an embodiment of a method for providing therapy to an individual.
Figure 4B:
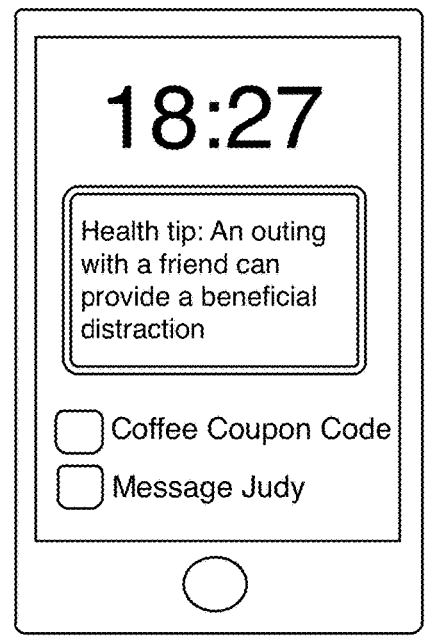

While Block S150 preferably includes a phone call-based period of communication for improving the psychological state of the individual, Block S150 can additionally or alternatively include promoting any other suitable form of communication (e.g., chat client-based communication, text messaging based communication, email-based communication, etc.), and/or any form of therapy to the individual based upon the analysis of Block S140. For instance, as shown in FIGS. 4A and 4B, Block S150 can include provision of a health-improving tip (e.g., a text-based health-improving tip, an audio clip of a health-improving tip, a visual health tip, etc.) to the individual (e.g., at a display of the mobile computing device, using a speaker of the mobile computing device, etc.), which is configured to improve the psychological state of the individual. Such forms of therapy can be provided if the individual does not elect the period of communication, if communication is not convenient, or if any other suitable factor deems phone call-based communication inappropriate.

Figure 3A:
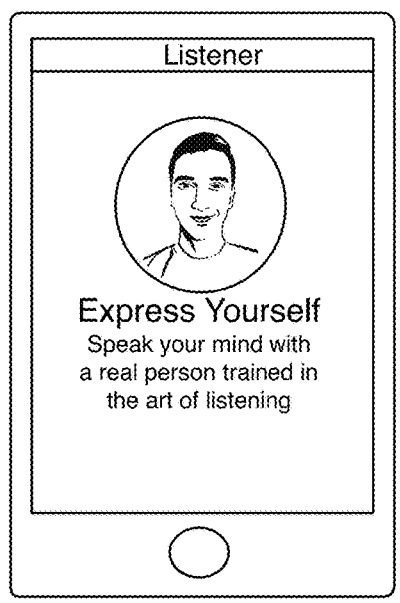
FIGS. 3A-3H depict an example of a method and system for providing therapy to an individual.
Figure 3B:
Figure 3C:
Figure 3D:
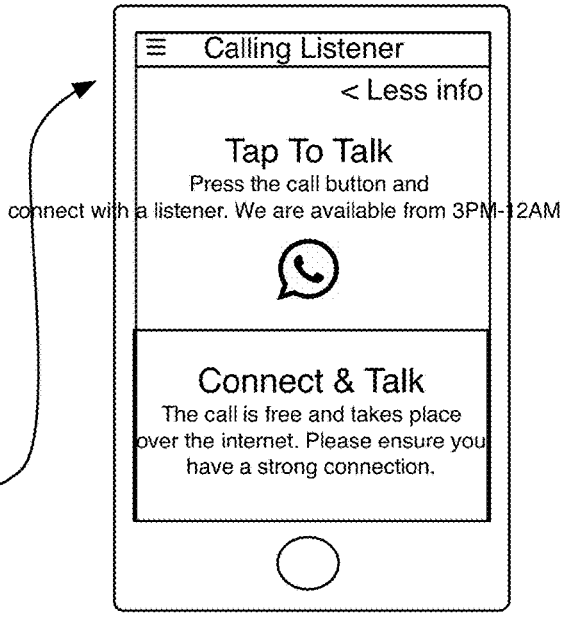
Figure 3E:
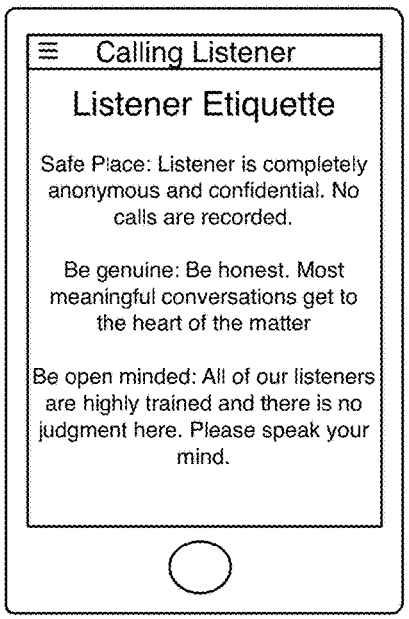
Figure 3F:
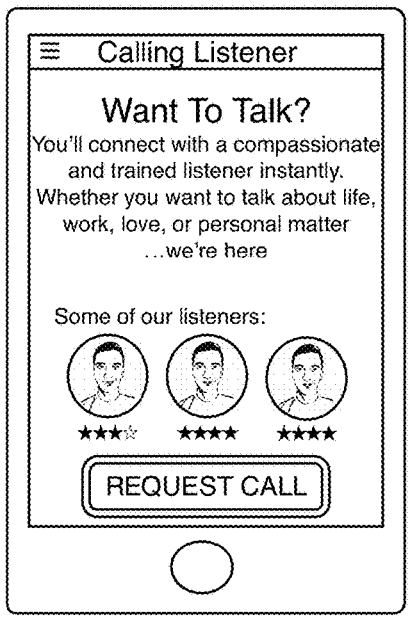
Figure 3G:
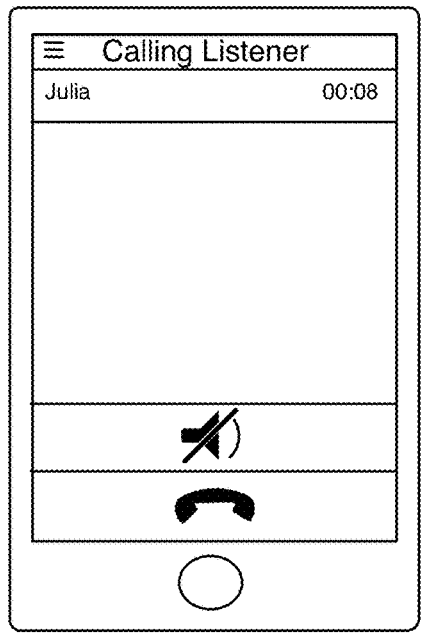
Figure 5G:
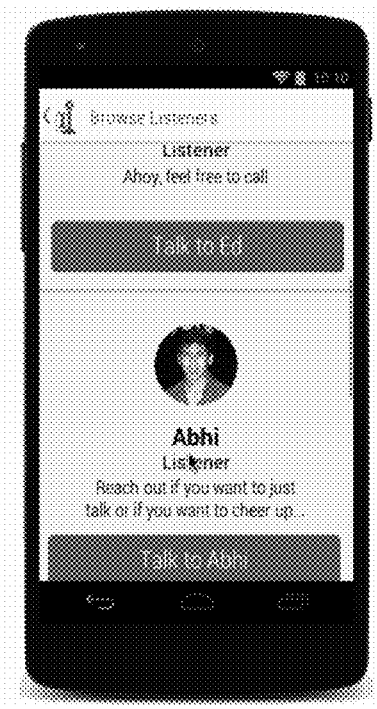
Figure 5H:
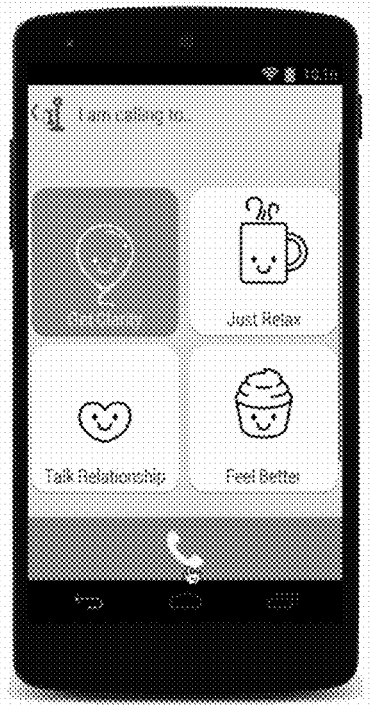
Figure 5I:
Figure 7:
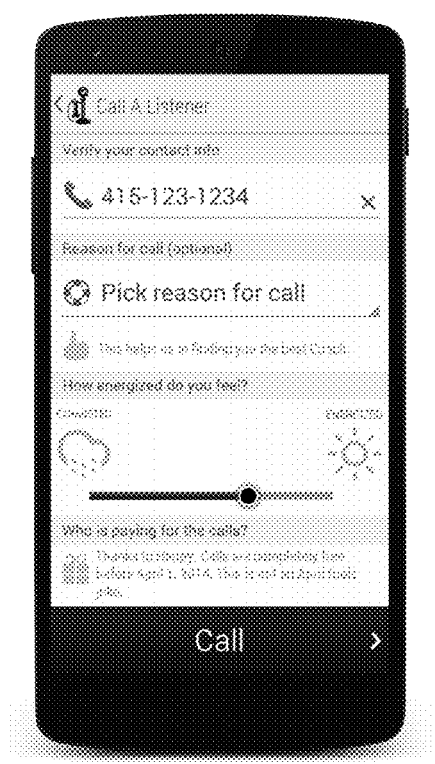
FIG. 7 depicts an example of a portion of a method for providing therapy to an individual.

As indicated above, Block S150 can include establishing the period of communication between the individual and a therapeutic entity, if promotion of communication is supported by an output of the analysis of Block S140. Establishing communication is preferably facilitated by a native application executing at the mobile computing device of the individual, wherein the native application interfaces with calling and/or other communication functions of the mobile computing device (e.g., as shown in FIG. 3F); however, establishing communication can alternatively be performed in any other suitable manner. Furthermore, in variations of Block S150, the individual can be provided with an option to self-elect a period of therapeutic communication, regardless of results of the analysis of Block S140. As such, the individual can establish a period of communication with a therapeutic entity even if communication promotion is not triggered by an output of Block S140. Whether or not the period of communication is initiated by election of the individual or promoted due to the analysis of Block S140, the individual can be prompted, before the period of communication, to provide some information pertaining to the reason for communication (e.g., to get clarity, to just relax, to talk about relationship issues, to talk about loss of a loved one, to feel better, etc.), as shown in FIGS. 5H and 7. Such information can facilitate matching of the individual to one of a set of therapeutic entities, and can additionally or alternatively be shared with the therapeutic entity to prepare the therapeutic entity for the period of communication.

Figure 5J:
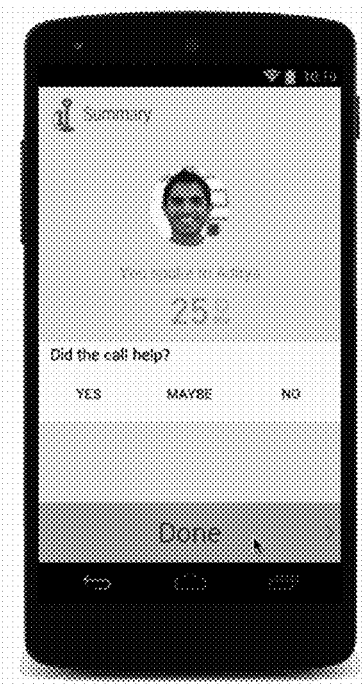
Figure 6A:
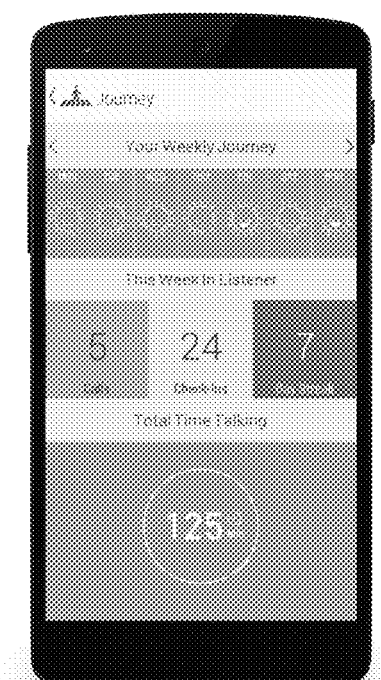
FIGS. 6A-6B depict examples of a portion of a method for providing therapy to an individual.
Figure 6B:

In examples of the method 100 including Block S150, as shown in FIGS. 3A-3H and 5A-5J, the individual can be prompted textually and visually through an application executing on a mobile computing device, using a display of the mobile computing device. In the example, election of communication by the individual (e.g., by interfacing with a touch screen of the mobile computing device), brings up an additional prompt, as shown in FIGS. 3F and 5G, that allows the individual to select one of a set of entities, wherein information about each of the set of entities, including name, appearance, gender, profession, and rating is shared with the individual from within the application. In the examples, a history of periods of communication, including a weekly calendar and metrics pertaining to the periods of communication (e.g., number of calls, number of "check-ins", a streak of days over which the individual communicated or did not communicate with a therapeutic entity, a total call time, etc.) can be provided to the individual from within the application, as shown in FIGS. 6A and 6B. Furthermore, metrics pertaining to the periods of communication can, in some variations, be used to provide rewards (e.g., coupons, monetary awards, discounted services, etc.) to the individual, and facilitate tracking of effectiveness (e.g., short-term effectiveness, long-term effectiveness) of therapy provided to the individual.

Figure 3H:
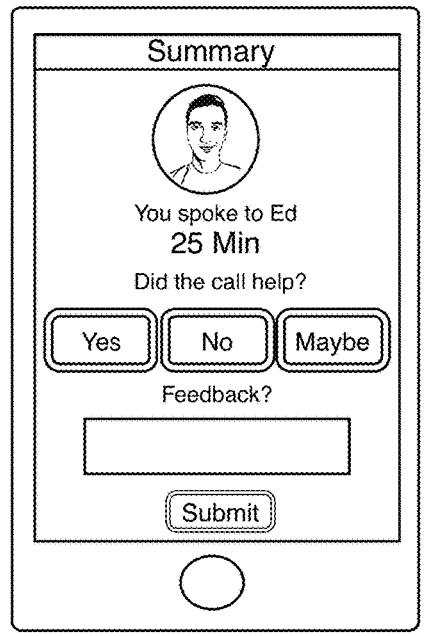

Block S160 recites: receiving feedback from the individual pertaining to the therapeutic entity and feedback from the therapeutic entity pertaining to the individual, upon completion of the period of communication. Block S160 functions to generate information pertaining to the individual and information pertaining to performance of the therapeutic entity, which can be used to improve interactions between individuals and therapeutic entities in subsequent implementations of blocks of the method 100. Such information can be used to identify communication features and/or other features that are effective in matching individuals with therapeutic entities, according to variations of the method 100 including Blocks S170, S180, and/or S190, as described in further detail below. In one variation, upon completion of a period of communication, the individual and the therapeutic entity can each be provided with a survey (e.g., an in-application survey) at which each entity can provide responses describing aspects of the period of communication. In a specific example, as shown in FIGS. 3H and 5J, the individual is provided with an in-application survey, displayed at a display of the mobile computing device upon completion of a period of communication with the therapeutic entity, wherein the in-application survey includes the duration of the period of communication, prompts the user to rate effectiveness of the communication, allows the user to rate how he/she felt before, during, and after the period of communication, and allows the individual to provide customized text feedback regarding other aspects of communication with the therapeutic entity. In the specific example, the therapeutic entity is also provided with a survey that allows the therapeutic entity to rate the interaction with the individual, to document observed psychological states of the individual during the period of communication, and to provide customized text feedback regarding other aspects of communication with the individual.

However, in some variations of Block S160, only one of the individual and the therapeutic entity participating in a period of communication may be prompted to provide feedback about the other participant in the period of communication. Additionally or alternatively, feedback can include self-rating feedback provided by the individual and/or the therapeutic entity participating in the period of communication.

In some variations, the method 100 can further include Block S170, which recites: determining a set of communication features based upon processing feedback from the individual pertaining to the therapeutic entity and feedback from the therapeutic entity pertaining to the individual. Block S170 functions to identify candidate features that can be used to improve matching of individuals with therapeutic entities, according to the matching model generated in Block S180. In Block S170, the set of communication features can include therapeutic entity-related features derived from any one or more of: communication length, rating of the therapeutic entity by the individual, a combination of communication length and rating of the therapeutic entity (e.g., a feature describing effectiveness vs. time for a period of communication), duration of the period of communication over which the therapeutic entity was listening, duration of the period of communication over which the therapeutic entity was speaking, attributes of the therapeutic entity (e.g., gender, experience, expertise, age, training, etc.), communication topic(s) handled, and any other suitable feature related to the therapeutic entity. In Block S170, the set of communication features can additionally or alternatively include individual-related features derived from any one or more of: demographic features of the individual (e.g., gender, possible disorders or conditions, preliminary diagnoses of conditions), severity of psychological state(s) exhibited by the individual during the period of communication, duration of the period of communication over which the individual was listening, duration of the period of communication over which the individual was speaking, openness of the individual during the period of communication, topics discussed by the individual during the period of communication, trends in types of therapeutic entities selected by the individual, communication length, self-assessed psychological state of the individual prior to the period of communication, self-assessed psychological state of the individual after to the period of communication, location of the individual during the period of communication, and any other suitable feature related to the individual. Furthermore, features of the set of communication features can include any suitable combination and/or weighting of any of the above features, or any other suitable feature generated based upon information derived from Blocks S110-S160 of the method 100.

The method 100 can further include Block S180, which recites: generating a matching model configured to identify candidate individual-therapeutic entity matches based upon the set of communication features. Block S180 functions to generate a matching model that can provide classifications of individuals and/or classifications of therapeutic entities, and effective matches between one or more classifications of individuals and classifications of therapeutic entities having high probability of providing therapeutic benefit to such individuals. In Block S180, the classification models and the matching model can be generated based upon identification of features associated with effective periods of communication, identification of features associated with neutral periods of communication (e.g., periods that neither improved nor worsened a psychological state of the individual), and/or identification of features associated with ineffective periods of communication (e.g., periods that contributed to a worse psychological state of the individual). In variations, a training dataset including historical data of candidate features related to individuals, therapeutic entities, and periods of communication, as associated with different classifications of effectiveness of the periods of communication. As such, in generating the model(s) of Block S180, the set of communication features identified in Block S170 can be ranked and/or narrowed to identify features most effective in classifying individuals, classifying therapeutic entities, and/or identifying effective matches between individuals and therapeutic entities. The models can be generated using any suitable correlational, statistical, and/or machine learning-based technique, as described in relation to Block S140 above, or using any other suitable technique.

In Block S180, identification of features attributed to effective, neutral, and/or ineffective periods of communication can further be used to improve training of one or more of the set of therapeutic entities. As such, insights derived from the model(s) of Block S180 can be used to improve effectiveness of the set of therapeutic entities. Additionally or alternatively, outputs of Block S180 can be used to adjust compensation provided to the therapeutic entities, as a performance incentive. Outputs of Block S180 can, however, be used in any other suitable manner.

The method 100 can further include Block S190, which recites: matching at least one of the individual and a second individual with one of a set of therapeutic entities, upon determining a second value of the psychological state parameter, based upon the matching model. Block S190 functions to intelligently identify effective matchings between individuals and therapeutic entities in order to increase effectiveness of a period of communication between the individual and a therapeutic entity. Thus, Block S190 preferably includes inputting features of the individual into the matching model of Block S180, and producing a matched therapeutic entity or set of matched therapeutic entities that could effectively provide beneficial communication to the individual. In some variations, Block S190 can function to establish a relationship between one or more therapeutic entities and one or more individuals, thereby providing an avenue for individuals to receive therapy from familiar, but otherwise anonymous entities. Additionally or alternatively, Block S190 can facilitate automatic establishment of a period of communication between the individual and a matched therapeutic entity, in more aggressive variations of the method 100, and given a level of trust in the matching model of Block S180. Variations of Block S190 can further produce additional data that can be used to refine the matching model of Block S180, thereby enhancing effectiveness of matches produced by the matching model.

1.5 Method—Therapeutic Coaching Entity

In some variations, one or more outputs of the above described method 100 can be used to facilitate, guide, or otherwise influence interactions between the individual and a therapeutic coaching entity, wherein the coaching entity functions to support one or more individuals associated with the method 100, reach out to individuals associated with the method 100 in times of need (as informed by data acquired from the individuals), and to triage individuals according to one or more measures of criticality. In relation to supporting individuals, the coaching entity can be the same entity or a different entity from the listening entity. As such, in some variations, the coaching entity can have functions that overlap with or otherwise extend beyond that of a listening entity. In other variations, the coaching entity can be the same as the listening entity.

In some variations, the coaching entity can function to listen to individuals and provide guidance, as well as to set goals for the individuals and facilitate determination of an appropriate treatment plan (e.g., traditional treatment plan, treatment plan involving responding to health-related advice, treatment plan involving a set of exercises for improving the state of the individual, etc.). In relation to reaching out to individuals, the coaching entity can function to provide positive reinforcement, to build a strong and on-going relationship with individuals as a critical contributor to improvement of the individual's state, to provide positive reinforcement of actions performed by the individuals, and/or to re-engage individuals who have reduced interaction with one or more system components associated with the method 100. In relation to triaging individuals, the coaching entity can function to monitor statuses of one or more individuals associated with the method 100, and/or to escalate individuals to a higher level of care (e.g., to interact with a licensed therapist, to provide medication support, etc.). All of these functions can be supported by analysis and processing of data acquired from the individuals, as described in more detail below.

As such, the coaching entity can be a mentor who motivates individuals associated with the method 100 to cultivate positive health choices, by assisting the individuals to become active participants in their health and well-being, and to achieve their health goals as facilitated by analysis and processing of data acquired from the individuals in the blocks of the method 100 described above and below. One or more functions of the coaching entity can include: providing information and education about mental health, helping individuals manage the emotional impact of health concerns, partnering with individuals to set goals, recommending strategies to help reach goals, helping identify challenges that could keep individuals from becoming healthier and suggesting ways to avoid them, helping individuals identify other sources of support, providing information to individuals to help them self-manage their mental health, developing strategies to help ensure follow through on care plans, connecting the individual with various tools for self-management (e.g., health tips, exercises) executed within a mobile application associated with the method 100, and helping individuals manage their concerns in relation to interactions with system components associated with the method 100. In one implementation, as supported by processing of data acquired according to the method 100, the coaching entity can help an individual to articulate and clarify problems/need for changes or improvement, can help an individual determine if there is a clear healthy life goal, can brainstorm potential actions to be taken, can (with data support) determine the action, can help the individual be accountable to the action, and can set a reasonable time frame for the individual to accomplish the action in achieving his/her goals. Additionally or alternatively, in implementation, the coaching entity can be trained to provide psychotherapeutic intervention to the individual(s), wherein, in examples, psychotherapy involves leveraging knowledge gained from exploring past behaviors and experiences of the individuals(s), in order to effect change in the present and/or the future for the individual(s). Psychotherapeutic intervention, in coordination with coaching, can thus be indicated for individuals with severe symptoms and/or low function, or where substance abuse is a presenting issue.

Regarding the therapeutic entity of Blocks S150-S190 above, the coaching entity can be the same entity or, alternatively, a different entity from the therapeutic entity (e.g., listening entity) of Blocks S150-S190 described above.

Figure 8:
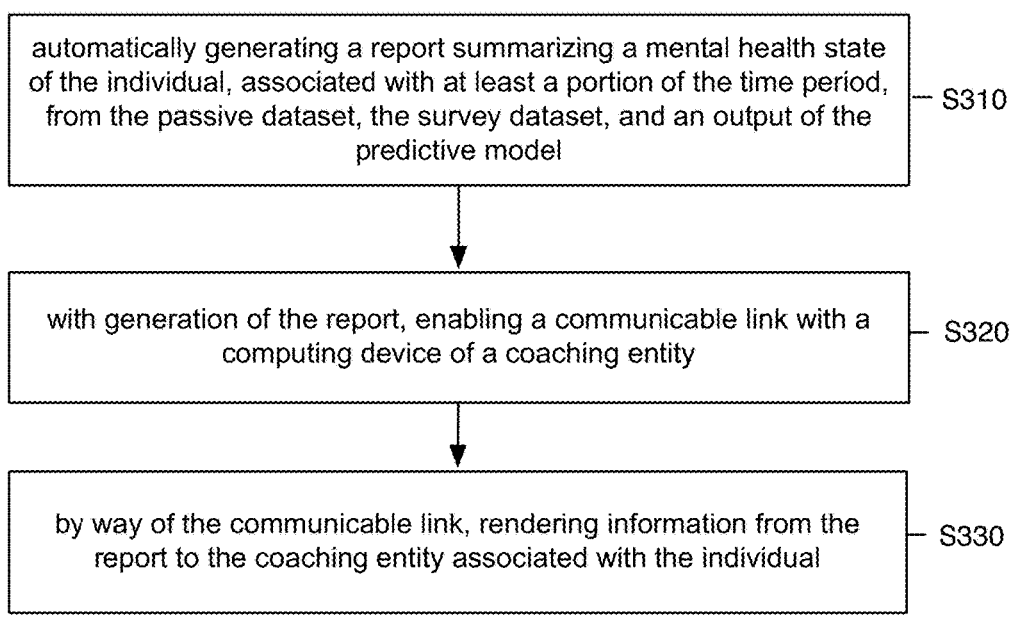
FIG. 8 is a flowchart of a portion of a variation of a method for providing therapy to an individual.

As such, in some variations, the method 100 can include Block S310, which recites: automatically generating a report summarizing a mental health state of the individual, associated with at least a portion of the time period, from the passive dataset, the survey dataset, and an output of the predictive model. As shown in FIG. 8, in relation to Block S310, the method 100 can additionally or alternatively include one or more of: Block S320, which recites: with generation of the report, enabling a communicable link with a computing device of a coaching entity; and Block S330, which recites: by way of the communicable link, rendering information from the report to the coaching entity associated with the individual, thereby enabling the coach to facilitate provision of a therapeutic intervention for the individual by way of at least one of the computing system and the mobile device of the individual.

In one implementation, Block S310 can include transforming data from one or more of the passive dataset, the survey dataset, and outputs of the predictive model into a report that can enable the coach to perform one or more functions in promoting the health of the individual. Block S130 can function to enhance the coaching entity's ability to deliver appropriate care to the individual(s) associated with the coaching entity, to decrease the coaching entity's burden, and to increase the efficiency of the coaching entity. The report(s) generated using Block S310 of the method 100 can be used during initial conversations, subsequent conversations, and/or proactive monitoring of the individual(s) associated with the coaching entity. Furthermore, the report(s) generate by Block S310 can include an individualized report corresponding to an individual associated with the coaching entity, and a population report corresponding to the totality of individuals associated with a coaching entity.

In variations, an individualized report can include information related to one or more of: contextual information of the coaching entity (e.g., coach name, coach identification code); a summary of contextual information of the individual (e.g., individual name, individual identification code, demographic information, diagnoses, medications, and patient notes); relevant metrics from the survey dataset (e.g., PHQ-9 scores, PHQ-9 score trends over time); relevant outputs derived from passive data and/or predictive models; goals of the individual and indications of progress in achieving such goals; tasks (e.g., assigned tasks, unassigned tasks) intended to be performed by the individual and indications of progress in achieving such tasks; status(es) of the symptom(s) of the individual in relation to health state (e.g., indications of suicidal ideation, etc.); decision criteria (e.g., including level of engagement of the individual) for reaching out to the individual; notes (e.g., a list of notes that the coaching can update for use in delivering follow up care); treatment plan information (e.g., therapists, medications) associated with the individual; and any other suitable information pertaining to the individual.

Figure 9A:
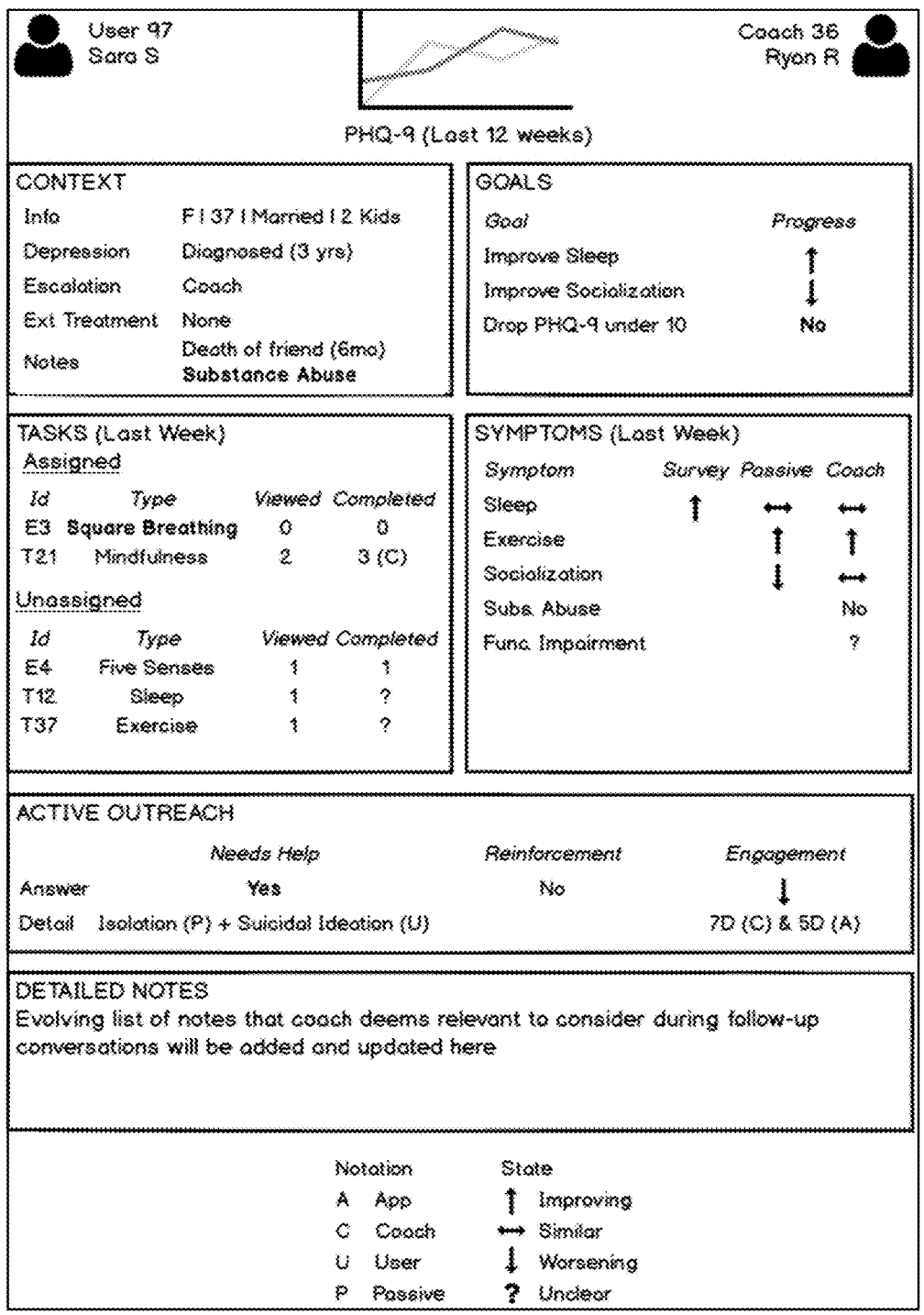
FIGS. 9A-9G depict examples of individualized reports provided to an entity associated with an individual in an embodiment of a method for providing therapy to an individual.

In a first specific example of an individualized report, as shown in FIG. 9A, the report can include: an individual's name and identification code; the coaching entity's name and identification code; trend in PHQ-9 scores for a duration of time (e.g., for the past 12 weeks); contextual information pertaining to the individual including gender, age, marital status, number of children, diagnosed mental conditions, escalation level (e.g., self management, engagement with a coaching entity, engagement with a licensed therapist, etc.), types of external treatment (e.g., medications), and notes (e.g., life events potentially resulting from or triggering the mental condition(s) of the individual); a list of goals for the individual including a sleep improvement goal with an indication of state in achieving the goal, a socialization improvement goal with an indication of state in achieving the goal, and a goal to lower PHQ-9 score with an indication of state in achieving the goal; a list of assigned and unassigned tasks (e.g., meditation task, mindfulness task, sensory awareness task, sleep improvement task, exercise task, etc.) to be completed by the individual, along with state of completion; a list of symptoms of the individual from a previous time period (e.g., the previous week) including sleep, exercise, socialization, substance abuse, and functional impairment, along with an indication of the state of improvement of the symptom and the source from which the status of the symptom was obtained (e.g., from a survey dataset, from a passive dataset, from the coaching entity, etc.); a list of criteria (e.g., the individual has reached a critical state of a mental health condition and needs help, the individual's relationship with the coaching entity should be reinforced, the individual's engagement with the mobile application has decreased, etc.) for actively reaching out to the individual by the coaching entity with suggested actions for the coaching entity and detailed reasons for the suggested actions (e.g., the individual exhibits suicidal ideation, the individual exhibits isolation, the individual's engagement with the coaching entity and the mobile application has decreased, etc.); and detailed notes regarding the individual.

Figure 9B:
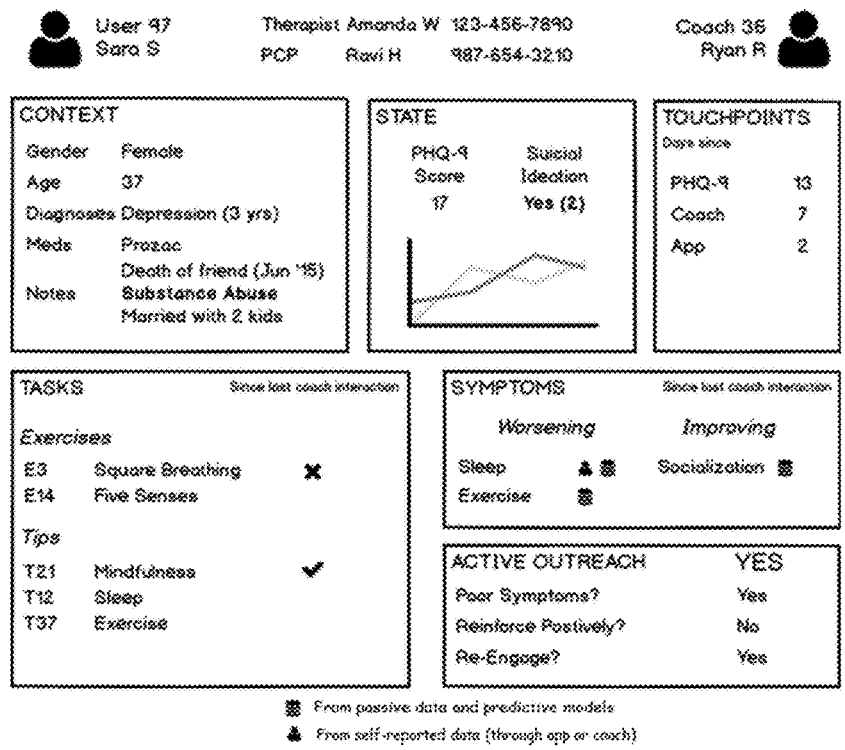

In a second specific example of an individualized report, as shown in FIG. 9B, the report can include: an individual's name and identification code; the coaching entity's name and identification code; the individual's licensed therapist and contact information; the individual's patient care provider and contact information; contextual information pertaining to the individual including gender, age, diagnosed mental conditions, types of external treatment (e.g., medications), and notes (e.g., life events potentially resulting from or triggering the mental condition(s) of the individual); trend in PHQ-9 scores for a duration of time (e.g., for the past 12 weeks); an indication of exhibition of suicidal ideation by the individual; an indication of the number of days since the individual has taken a PHQ-9 assessment, engaged with the coaching entity, and engaged with the mobile application associated with the method 100; a list of assigned and unassigned tasks (e.g., meditation task, mindfulness task, sensory awareness task, sleep improvement task, exercise task, etc.) to be completed by the individual, along with state of completion; a list of symptoms of the individual from a previous time period (e.g., since the last time of engagement with the coaching entity) including sleep, exercise, socialization, substance abuse, and functional impairment, along with an indication of the state of improvement of the symptom, and indications of the source(s) from which the symptom states were determined or observed (e.g., from passive data, from predictive models, from survey data, from the coaching entity, etc.); and recommendations for the coaching entity to actively reach out to the individual based on exhibition of poor symptoms by the individual, need for positive reinforcement of behaviors of the individual, an indication of momentum of the individual in engaging with the mobile application and/or the coaching entity, and need for re-engaging the individual.

Figure 9C:
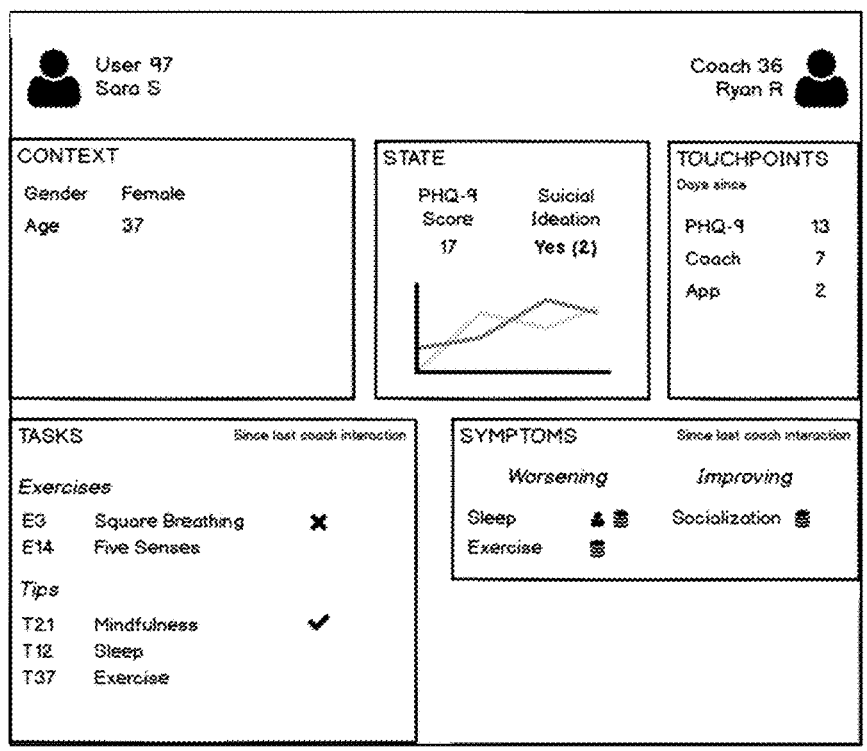

In a third specific example of an individualized report, as shown in FIG. 9C, the report can include: an individual's name and identification code; the coaching entity's name and identification code; contextual information pertaining to the individual including gender and age; trend in PHQ-9 scores for a duration of time (e.g., for the past 12 weeks); an indication of exhibition of suicidal ideation by the individual; an indication of the number of days since the individual has taken a PHQ-9 assessment, engaged with the coaching entity, and engaged with the mobile application associated with the method 100; a list of assigned and unassigned tasks (e.g., meditation task, mindfulness task, sensory awareness task, sleep improvement task, exercise task, etc.) to be completed by the individual, along with state of completion; and a list of symptoms of the individual from a previous time period (e.g., since the last time of engagement with the coaching entity) including sleep, exercise, socialization, substance abuse, and functional impairment, along with an indication of the state of improvement of the symptom.

Figure 9D:
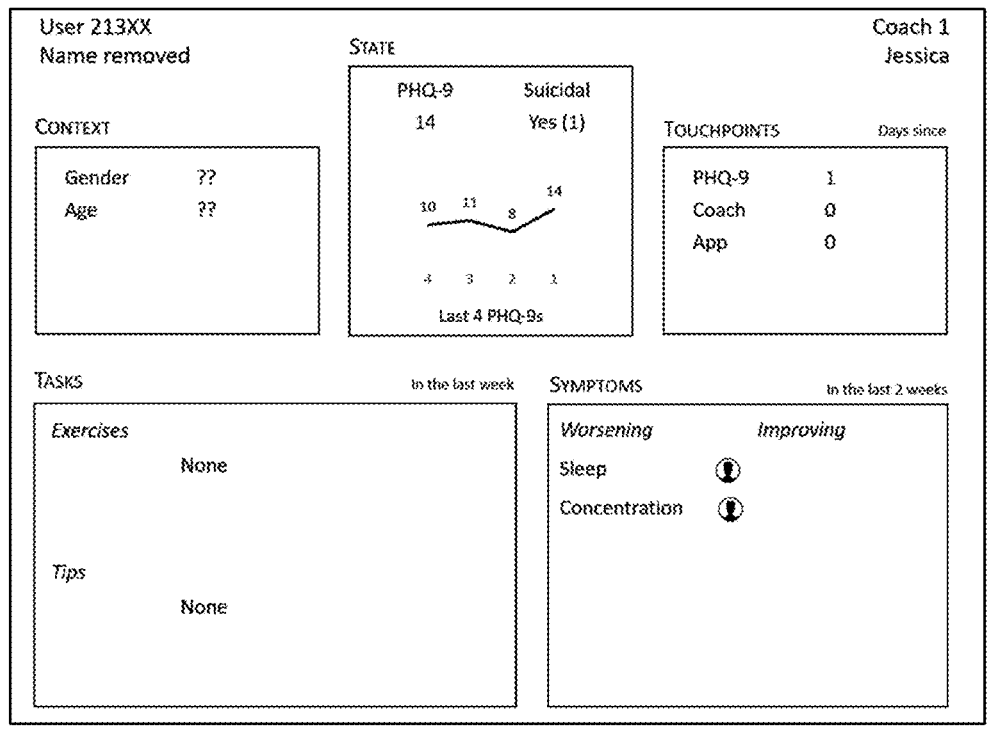
Figure 9E:
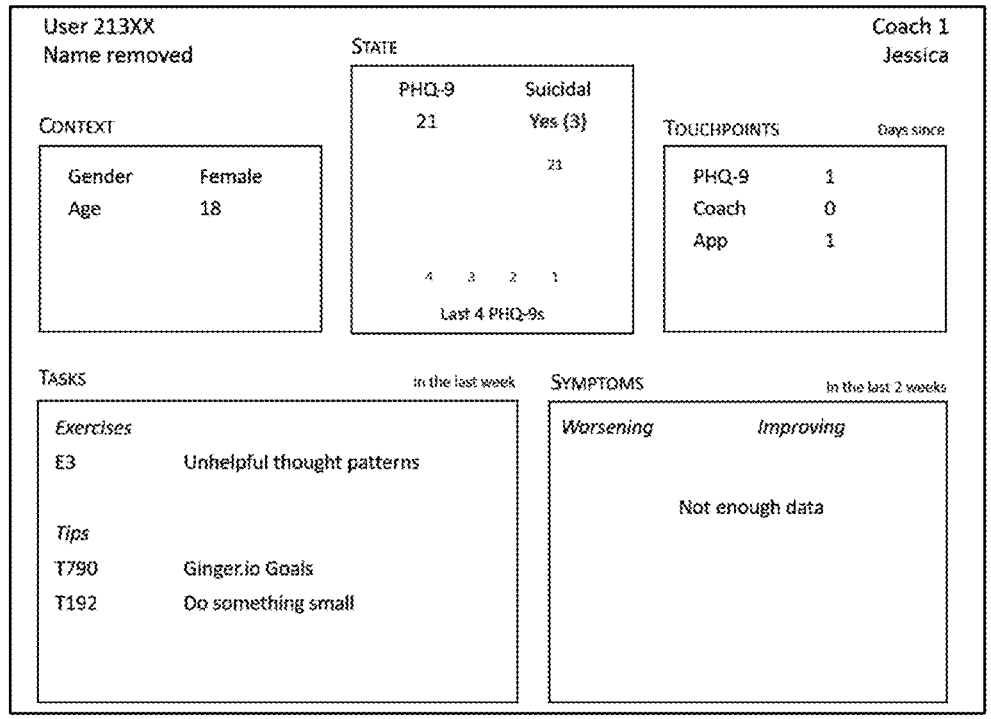

In fourth and fifth specific examples of an individualized report, as shown in FIGS. 9D and 9E, respectively, the report can include: an individual's name and identification code; the coaching entity's name and identification code; contextual information pertaining to the individual including gender and age; trend in PHQ-9 scores; an indication of exhibition of suicidal ideation by the individual; an indication of the number of days since the individual has taken a PHQ-9 assessment, engaged with the coaching entity, and engaged with the mobile application associated with the method 100; a list of assigned and unassigned tasks (e.g., meditation task, mindfulness task, sensory awareness task, sleep improvement task, exercise task, etc.) to be completed by the individual, along with state of completion; and a list of symptoms of the individual from a previous time period (e.g., since the last time of engagement with the coaching entity) including sleep, exercise, socialization, substance abuse, and functional impairment, along with an indication of the state of improvement of the symptom.

Figure 9F:
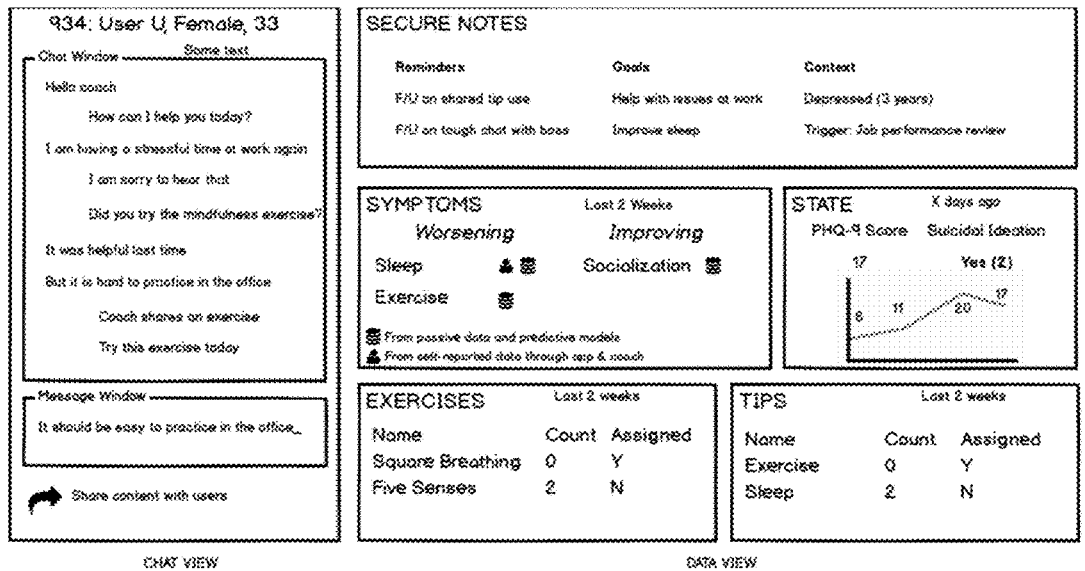
Figure 9G:
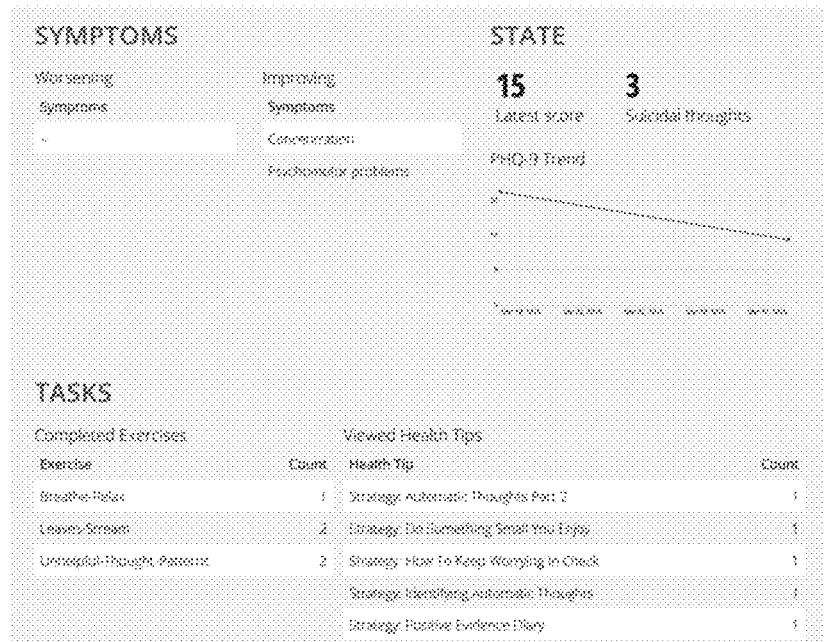

A sixth specific example of an individualized report/dashboard, as shown in FIGS. 9F and 9G, can include an individual's identification code; a chat client tool (e.g., live chat window) for communication with the individual; a message client tool (e.g., a message window) for sending messages with the individual and/or other individuals associated with the coaching entity; a notes section for summarizing reminders pertaining to activities of the individual, goals of the individual, and history of the individual; a list of symptoms of the individual (e.g., sleep, exercise, socialization, substance abuse, and functional impairment), along with an indication of the state of improvement of the symptom (e.g., worsening vs. improving, and indications of the source(s) from which the symptom states were determined or observed (e.g., from passive data, from predictive models, from survey data, from the coaching entity, etc.); trend in PHQ-9 scores; an indication of exhibition of suicidal ideation by the individual; a list of assigned and unassigned tasks (e.g., meditation task, mindfulness task, sensory awareness task, sleep improvement task, exercise task, etc.) to be completed by the individual, along with state of completion; and a list of health advice pieces viewed by the individual.

In variations, a population report can provide a view of the population of individuals managed by the coaching entity, and include information related to one or more of: depression trends and/or other health-related trends of an individual over time; assessments by one or more of the coaching entity and/or a licensed therapist for each individual over time; predictions of anticipated states of the individuals (e.g., based upon outputs of Blocks S110-S140); status(es) of the symptom(s) of the individual in relation to health state (e.g., indications of suicidal ideation, etc.); statuses indicative of need for escalation of individuals to higher levels of care; risk factors for each individual; recommendations for the coaching entity to reach out to one or more individuals; and any other suitable information.

As shown in FIG. 10A, a first specific example of a population report tool for the coaching entity can include: a list of all individuals (e.g., with name and identification code) associated with the coaching entity; a current PHQ-9 score for each individual; a time period associated with PHQ-9 scores for the individual; an indication of mental condition trend (e.g., improving, similar, worsening, unclear, etc.) for the individuals, an indication of the number of days during which each individual engaged with the coaching entity; a rating of the coach by each individual; an indication of whether or not each individual engaged with a therapist and for how long; a rating of therapists by each individual; an indication of the number of days during which each individual engaged with the mobile application associated with the method 100; an indication of a predicted state of each individual based on passive data; an indicated escalation state (e.g., self management, engagement with a coaching entity, engagement with a licensed therapist, etc.) for each individual; risk factors (e.g., poor sleep, substance abuse, high PHQ-9 score, suicidal ideation) for each individual; and a recommendation for actively reaching out to each individual.

As shown in FIG. 10B, a second specific example of a population report tool for the coaching entity can include: a list of all individuals associated with the coaching entity (e.g., with user identification codes); active outreach needs of each individual; a number of days associated with active outreach for each individual; indication of exhibition of suicidal ideation for each individual (e.g., number of instances of suicidal ideation); outreach priority for each individual; number of unread messages for each individual; and a duration of time since the last message was sent to each individual.

Figure 10C:
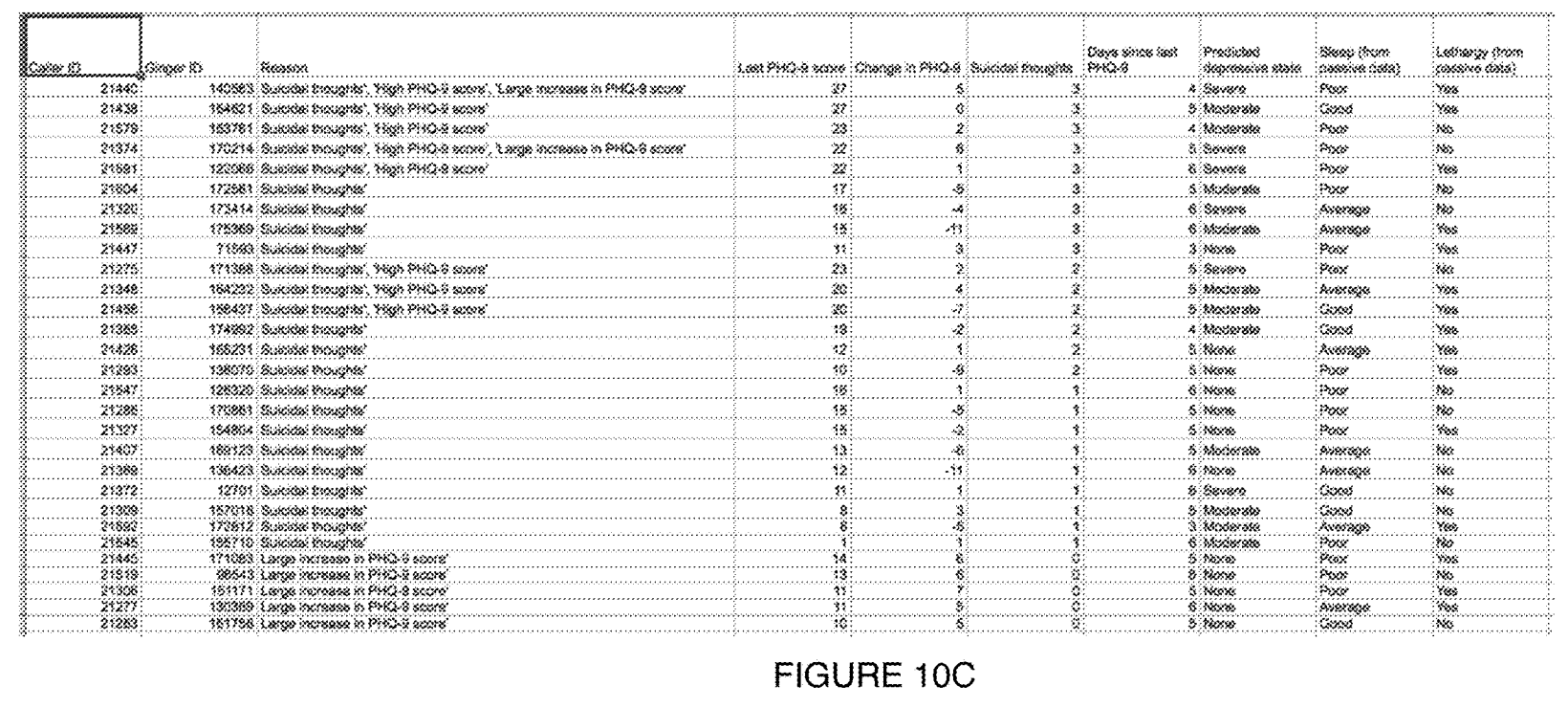

As shown in FIG. 10C, a third specific example of a report can include a list of individuals for whom active outreach is recommended, including user identification codes; a reason for the recommendation for reaching out to the individual; the most recent PHQ-9 score, change in PHQ-9 score; indication of suicidal thoughts/ideation; an indication of the number of days since the last PHQ-9 assessment occurred; relevant outputs of predictive models (e.g., predicted depressive state for each individual); and relevant outputs derived from passive data (e.g., sleep behavior of each individual, lethargy of each individual, mobility of each individual, etc.).

Figure 10D:
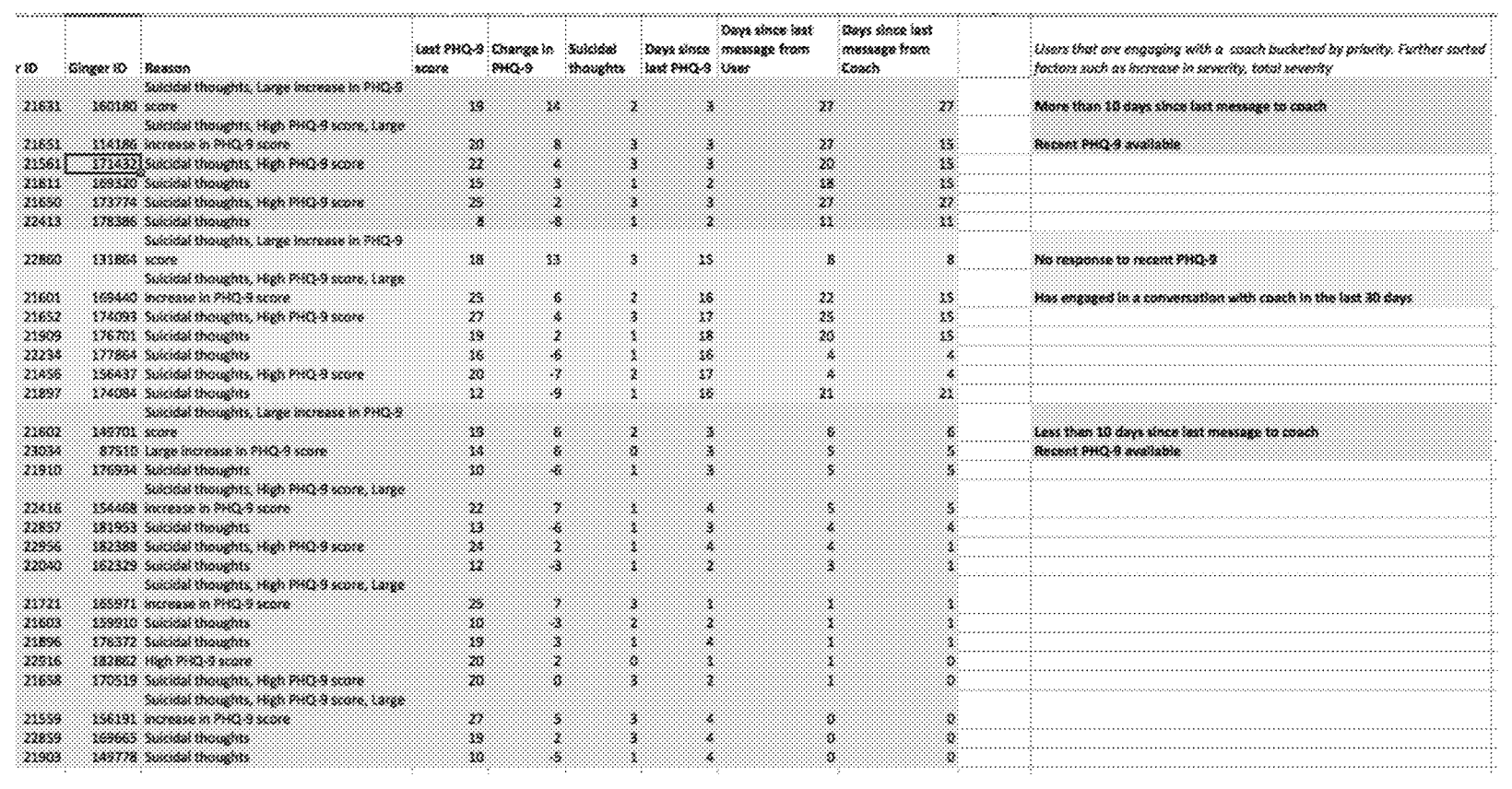

In the variation of FIG. 10C shown in FIG. 10D, individuals associated with the coaching entity can be grouped according priority. For instance, individuals who have not communicated with the coaching entity for above a threshold duration of time (e.g., 10 days), with recent PHQ-9 scores may grouped according to a first level of priority for outreach, individuals who have not responded to recent requests to take a PHQ-9 assessment, but who have engaged with the coaching entity within a threshold duration of time (e.g., last 30 days) can be grouped according to a second level of priority for outreach, and individuals who have communicated with the coaching entity within a threshold duration of time (e.g., 10 days) and who have recently taken a PHQ-9 assessment can be grouped according to a third level of priority for outreach.

As such, in relation to the above described coaching entity functions of supporting individuals, reaching out to individuals, and triaging individuals, and triaging individuals, the reports generated using instances of Block S310 of the method 100 and/or processing of data acquired from Blocks S110-S140 of the method 100 can be used to: provide context for supporting individuals (e.g., in terms of recalling past interactions with an individual, in terms of progress of an individual in reaching a goal, in terms of progress of an individual in improving mental health state); increase efficiency in providing support for individuals (e.g., by notifying the coaching individual of any mental health-related statuses of the individuals pertaining to exercise, sleep, relationships, symptoms, and any other suitable factor); facilitate making of decisions by the coaching entity; automate reaching out to individuals by the coaching entity in times of need (e.g., by automatically establishing a communication between the coaching entity and an individual with a messaging or phone calling client); automate reaching out to individuals for positive reinforcement of behaviors; automate reaching out to individuals for re-engagement with system components associated with the method 100; automate adjustment to proposed treatment plans for individuals; provide decision making support or automation in relation to triaging individuals according to criticality of state; increase efficiency in triaging individuals; and perform any other suitable function.

Figure 11A:
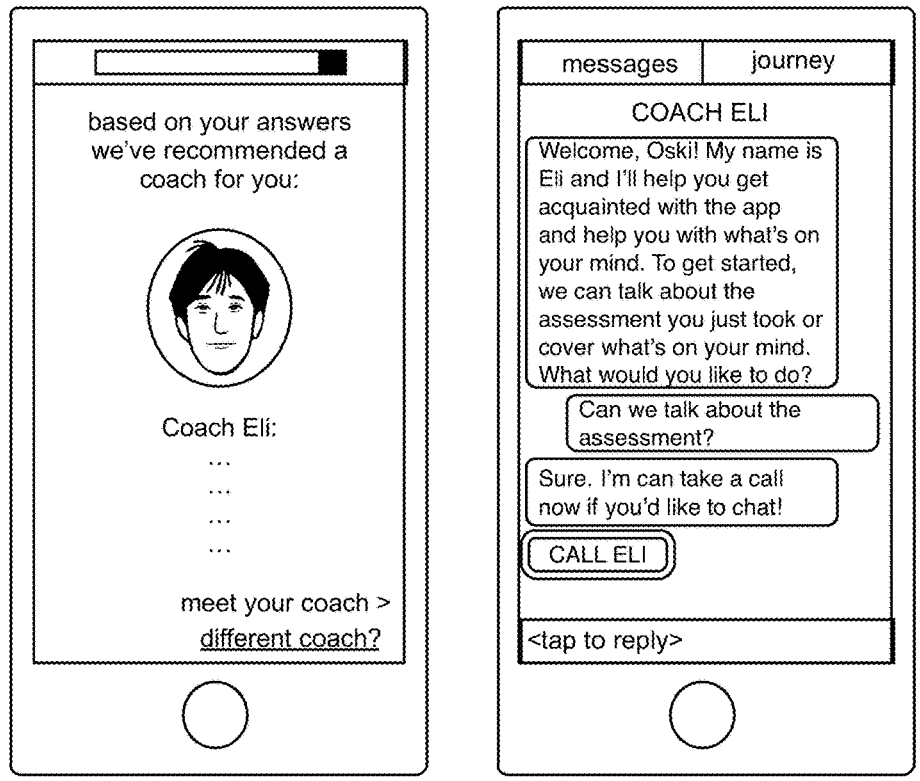
FIG. 11A depicts an example interaction with a coaching entity within a mobile application experience in an embodiment of a method for providing therapy to an individual.

Block S320 recites: with generation of the report, enabling a communicable link with a computing device of the coaching entity, which functions to enable transmission of information from the report to the coaching entity associated with the individual. As shown in the example of FIG. 11A, the coaching entity can be matched with the individual based upon data acquired from the individual (e.g., using an appropriate matching model), and Block S320 can enable a communicable link for transmission of information from generated reports to the coaching entity, which allows the coaching entity to provide appropriate care for the individual. Similar to above described blocks of the method 100, the communicable link can be a wired and/or wireless data link (e.g., a communicable link over Bluetooth, a communicable link over Bluetooth LTE, etc.) by which information from the report can be transmitted from the computing system to a device of the coaching entity. However, Block S320 can include another other suitable variation of enabling a communicable link with a computing device of the coaching entity.

Block S330 recites: by way of the communicable link, rendering information from the report to a coaching associated with the individual. Block S330 functions to provide the information from the report to the individual, in a digital format, thereby allowing the coaching entity to interact with the individual in an informed manner. Preferably, in Block S330, the report is rendered within an application (e.g., web accessible application, mobile application, etc.) that the coaching entity has privileges of access to. In variations, the application can provide the coaching entity with online tools for interacting with one or more individuals associated with the coaching entity, tools for modifying reports of one or more individuals associated with the coaching entity, tools for adjusting types of information presented in relation to individuals associated with the coaching entity, tools for appropriate adjustment of treatment plans of individuals associated with the coaching entity, and tools for escalating care of individuals associated with the coaching entity to a higher level of care (e.g., in relation to psychotherapy, in relation to clinical therapy, in relation to medication provision, etc.).

In one example of interactions between a coaching entity and an individual, the coaching entity can conduct multiple sessions with an individual needing help to improve a given state, and the coaching entity can receive reports generated by blocks of the method 100 over the span of interacting with the individual. In the example, the first session with the individual can be used to explain how the coaching entity can help the individual, set expectations of roles between the coaching entity and the individual, describe workflow of working with the coaching entity, generate a list of problems of the individual, identify an issue to focus on, and apply a problem solving approach for the issue identified. Subsequent sessions can then be used to build an alliance between the coaching entity and the individual, to monitor progress in dealing with issues, to identify any additional issues, to determine and/or modify treatment plans, and/or to provide any other suitable type of therapeutic guidance in improving health state.

1.6 Method—Escalation of Care for an Individual

In association with escalation of an individual to a higher level of care, the report(s) outputted using one or more blocks of the method 100 can be used by the coaching entity to triage patients according to one or more measures of criticality. In a specific implementation, an individual can be referred to therapy (e.g., psychotherapeutic intervention, medication referral) according to one or more of the following factors: low function (e.g., as determined from processing of data from the log of use and/or other data acquired according to the method 100); moderate-to-severe symptoms as assessed from the survey dataset (e.g., a PHQ-9 score above 15, etc.); evidence of current and/or past substance abuse; a detection of bringing of the past into conversations with the coaching entity; detected evidence of suicidal ideation (e.g., from interactions with the individuals, from processing of data); and any other suitable factor. In variations, triaging actions can include one or more of: transitioning an individual into interactions with a licensed therapist; guiding an individual to a hotline (e.g., a suicide hotline, a talk line, an emergency service); appropriate documentation of any instance of suicidal ideation, self harm, or homicidal ideation; and any other suitable action.

Figure 11B:
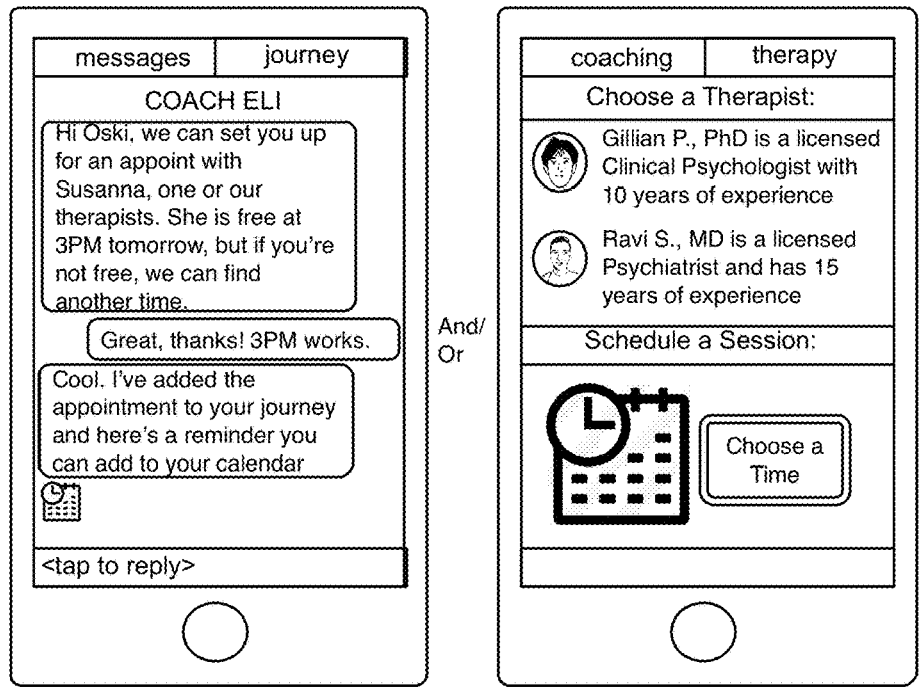
FIGS. 11B and 11C depict examples of escalation of care of an individual within a mobile application experience in an embodiment of a method for providing therapy to an individual.
Figure 11C:
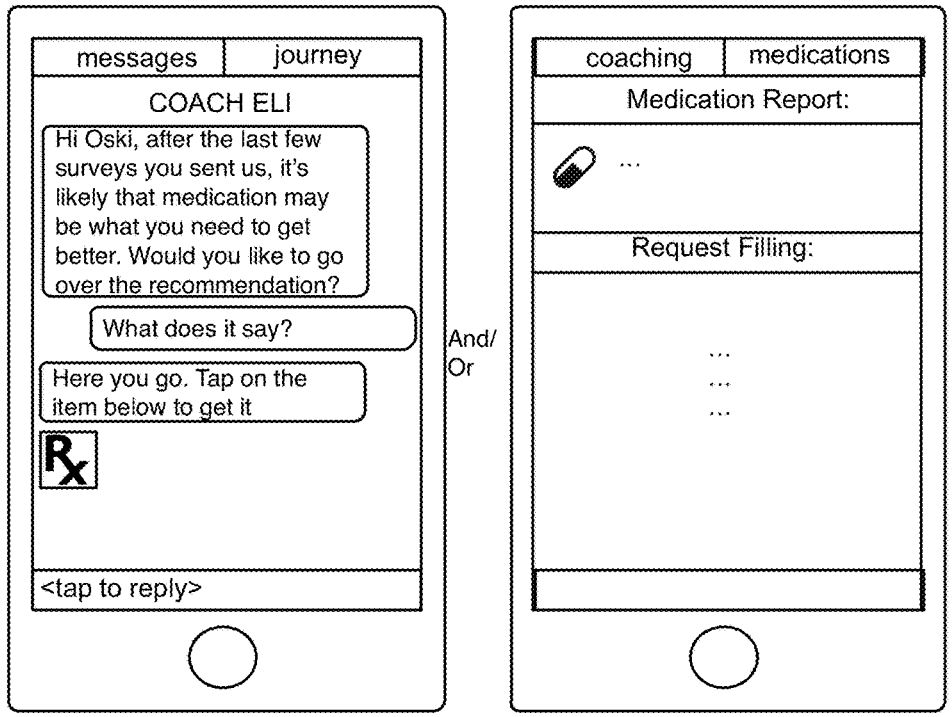

In the example shown in FIG. 11B, the coaching entity can, within a messaging client with an individual needing a higher level of care, connect the individual with a licensed therapist (e.g., an in-house therapist, an out-of-house therapist) and/or schedule a session between the individual and a licensed therapist associated with the method 100. In the example, the session can be implemented within the mobile application associated with the method 100, using a video chat feature of the mobile application. Additionally or alternatively, as shown in FIG. 11B (right), the individual can be presented with multiple licensed therapists as options, and can elect a specific licensed therapist he/she would like to engage with. In the example shown in FIG. 11C, the method 100 can additionally or alternatively include providing medication support to an individual needing a higher level of care. In more detail, outputs of Block S110-S140 can guide a coaching (or other) entity to inform the individual of the medication(s) he/she may need within a message client of the mobile application, and facilitate delivery of the medication(s) to the individual by a pharmacy. Escalation of care provided to an individual can, however, include implementation of any other features of the mobile application and any other suitable type of care.

Thus, the coaching entity can, as supported by the data transformation Blocks of the method 100, function to provide an intermediary between individuals needing therapy and a care team (e.g., clinical entities), and to facilitate delivery of a personalized treatment plan to individuals needing therapy, as backed by tools within a mobile application experience. In more detail, the coaching entity can provide human interaction as a driver of engagement and positive outcomes for individuals, can create a therapeutic alliance with the individual, and can support user with advance care (e.g., in an in-house manner) in a manner that is less complex for the user than current standards of care.

Figure 12A:
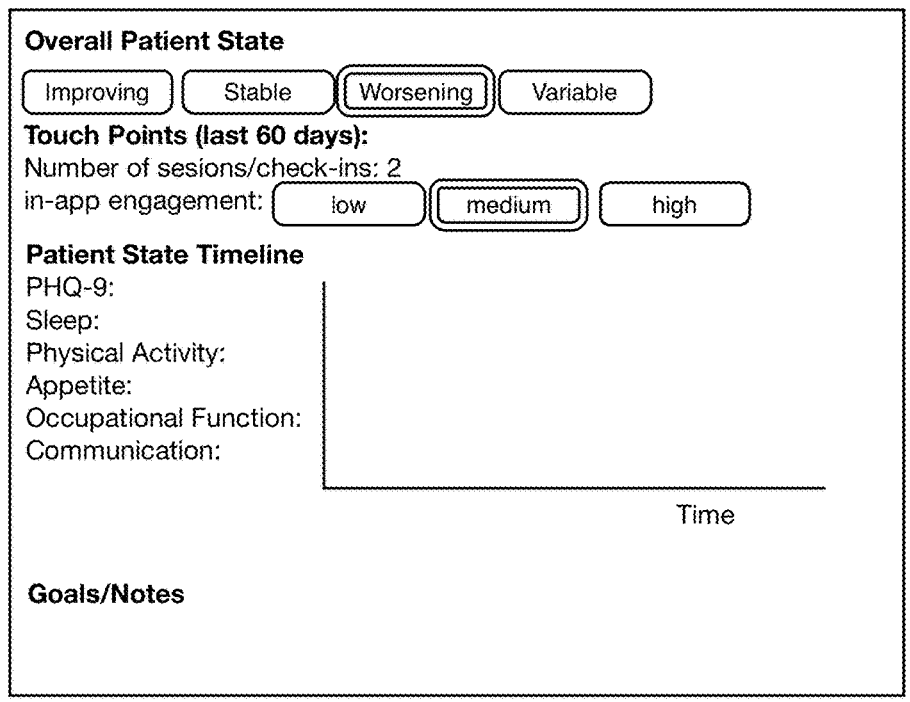

In relation to escalation of care, the method 100 can include blocks for generation of reports for licensed therapist and/or patient care providers analogous to those for generation of a report for a coaching entity. In a first example of a report for a licensed therapist, as shown in FIG. 12A, a report can include: an indication of overall patient state (e.g., improving state, stable state, worsening state, variable state, etc.); a number of touch points (e.g., for the past 60 days) with the patient in terms of number of sessions or check-ins with the patient and level of engagement with a mobile application associated with the method 100 (e.g., low level of engagement, medium level of engagement, high level of engagement, etc.); a timeline of patient events in different categories associated with the health condition of the patient (e.g., PHQ-9 scores, sleep symptoms, changes in physical activity, changes in appetite, changes in occupational function, changes in communication behavior, etc.); and notes and goals pertaining to the patient.

In a first example of a report for a primary care provider (PCP) associated with the individual, as shown in FIG. 12B, a report can include: contextual information pertaining to the patient including gender, age, ethnicity, marital status, number of children, occupational status, medical history, diagnosed mental conditions, history of substance abuse, and family history; trend in PHQ-9 scores for a duration of time (e.g., for the past 12 weeks); changes in symptoms (e.g., for the past two weeks), including changes in sleep behavior, exhibition of loss in interest in activities, exhibition of feelings of guilt or worthlessness, exhibition of lack of energy, exhibition of reduction in cognition or concentration, changes in appetite or weight loss, exhibition of psychomotor agitation or retardation, exhibition of suicide or death preoccupation thoughts, and other symptoms; medications currently taken by the patient; additional notes pertaining to behaviors of the patient; and a message to the physician associated with the patient. The PCP report could thus allow a PCP to facilitate provision of medications for an individual needing a higher level of care, according to the method 100.

The method 100 can include any other suitable blocks or steps configured to improve a psychological state of an individual by providing therapeutic communication to the individual in times of need. Furthermore, as a person skilled in the art will recognize from the previous detailed description and from the figures and claims, modifications and changes can be made to the method 100 without departing from the scope of the method 100.

2. System

Figure 13:
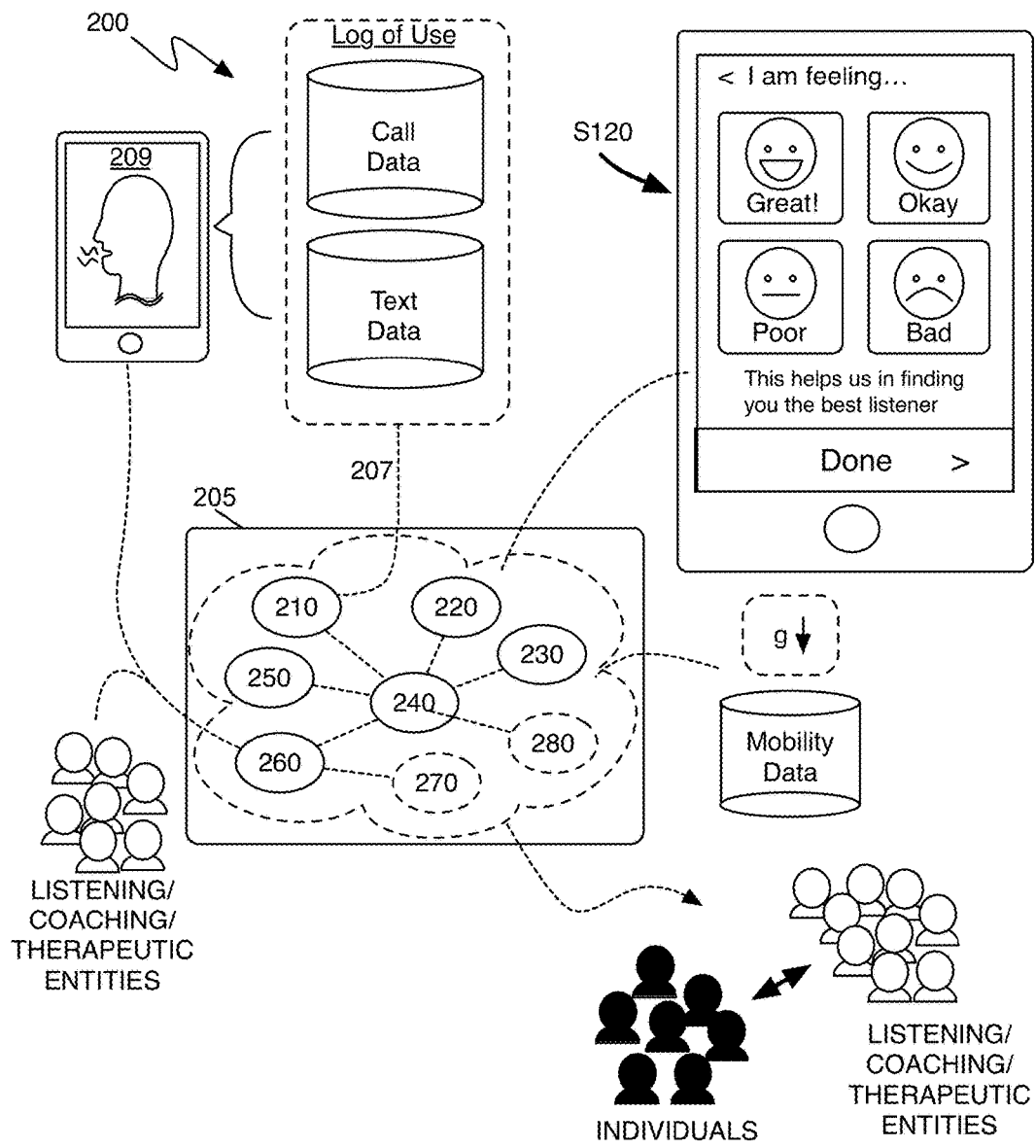
FIG. 13 depicts an embodiment of a system for providing therapy to an individual.

As shown in FIG. 13, a system 200 for providing therapy to an individual includes: a processing system 205 including: an interface 207 with a data collection application executing on a mobile computing device 209 of the individual; a first module 210 configured to access a log of use of a communication application coupled to the data collection application on the mobile computing device by the individual within a time period; a second module 220 configured to receive an input and/or a survey dataset, indicative of a self-assessed psychological state of the individual, by the individual at the mobile computing device; a third module 230 configured to receive a supplementary dataset characterizing activity of the individual in association with the time period; a fourth module 240 configured to transform data from the log of use, the input and/or the survey dataset, and the supplementary dataset into an analysis including a value of a mental health state parameter associated with the time point and indicative of a psychological state of the individual; a fifth module 250 configured to promote and establish a period of communication between the individual and a therapeutic entity, based upon the value of the psychological state parameter; and a sixth module 260 configured to receive feedback from the individual pertaining to the therapeutic entity and feedback from the therapeutic entity pertaining to the individual, upon completion of the period of communication. In some variations, the system can include a seventh module 270 configured to determine a set of communication features based upon processing feedback from the individual pertaining to the therapeutic entity and feedback from the therapeutic entity pertaining to the individual, and generate a matching model configured to identify candidate individual-therapeutic entity matches based upon the set of communication features. In some variations, the system can include an eighth module 280 configured to generate and transmit reports for entities in communication with the individual, as described in relation to Blocks S310-S330 above.

The system functions to perform at least a portion of the method 100 described in Section 1 above, but can additionally or alternatively be configured to perform any other suitable method for providing an avenue for therapeutic communication to an individual experiencing an adverse psychological state. The system 200 is preferably configured to facilitate reception and processing of a combination of passive data (e.g., unobtrusively collected communication behavior data, mobility data, etc.) and active data (e.g., inputs provided by individuals, post-communication survey responses), but can additionally or alternatively be configured to receive and/or process any other suitable type of data. As such, the processing system 205 can be implemented on one or more computing systems including one or more of: a cloud-based computing system (e.g., Amazon EC3), a mainframe computing system, a grid-computing system, and any other suitable computing system. Furthermore, reception of data by the processing system 205 can occur over a wired connection and/or wirelessly (e.g., over the Internet, directly from a natively application executing on an electronic device of the individual, indirectly from a remote database receiving data from a device of the individual, etc.).

The processing system 205 and data handling by the modules of the processing system 205 are preferably adherent to health-related privacy laws (e.g., HIPAA), and are preferably configured to privatize and/or anonymize individual data according to encryption protocols. In an example, when an individual installs and/or authorizes collection and transmission of personal communication data by the system 200 through the native data collection application, the native application can prompt the individual to create a profile or account. In the example, the account can be stored locally on the individual's mobile computing device 209, in a process as shown in FIGS. 3B, 5D, and 7, and/or remotely. Furthermore, data processed or produced by modules of the system 200 can be configured to facilitate storage of data locally (e.g., on the patent's mobile computing device, in a remote database), or in any other suitable manner. For example, private health state-related data can be stored temporarily on the individual's mobile computing device in a locked and encrypted file folder on integrated or removable memory. In this example, the individual's data can be encrypted and uploaded to the remote database once a secure Internet connection is established. However, individual data can be stored on any other local device or remote data in any other suitable way and transmitted between the two over any other connection via any other suitable communication and/or encryption protocol. As such, the modules of the system 200 can be configured to perform embodiments, variations, and examples of the method 100 described above, in a manner that adheres to privacy-related health regulations.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a individual computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for providing a therapy to an individual for an adverse mental health state, the method comprising:
   transmitting, from a communication module executing on a mobile device to a computing system, a log of use dataset associated with communication behavior of the individual during a time period, wherein the log of use dataset includes at least one of a phone calling component and a text messaging component;
   at the computing system, receiving a supplementary dataset characterizing activity of the individual in association with the time period;
   within an application executing at the mobile device, generating a survey dataset upon retrieving responses provided by the individual to at least one of a set of surveys, associated with a set of time points of the time period; and
   at the computing system 1) automatically determining a report summarizing the adverse mental health state of the individual, associated with at least a portion of the time period, from the supplementary dataset and the survey dataset, 2) with generation of the report, enabling a communicable link with a computing device of a coach, and 3) by way of the communicable link and the coach, administering the therapy based on information from the report to the associated with the individual, thereby enabling improvement of the adverse mental health state for the individual by way of at least one of the computing system and the mobile device.

2. The method of claim 1, wherein transmitting the log of use dataset further includes: at the computing system, extracting, from the log of use dataset: a length of text messages received by the individual from a close associate of the individual, a phone call duration, an incoming call count, and a number of ignored calls.

3. The method of claim 2, wherein receiving the supplementary dataset includes extracting a mobility radius associated with at least one time point of the time period and derived from global positioning sensors of the mobile communication device.

4. The method of claim 1, wherein generating the report includes transforming data from the supplementary dataset and the survey dataset into a trend in PHQ-9 scores over time, an indication of exhibition of suicidal ideation by the individual, and indication of time since the individual has engaged with the coach, a completion status for each of a set of mental health improvement tasks promoted to the individual, and a symptom progression status of each of a set of symptoms of the individual, thereby summarizing the adverse mental health state of the individual.

5. The method of claim 1, wherein generating the report includes transforming data from the supplementary dataset and the survey dataset into a recommendation for reaching out to the individual, with an analysis of: a level of engagement between the individual and the application, a level of engagement between the individual and the coach, a need for positive reinforcement of behaviors of the individual, and a comparison between a mental health state parameter a critical threshold.

6. The method of claim 5, wherein in response to the analysis, the method further includes automatically prompting the coach to establish communication with the individual using a user interface of the computing device of the coach.

7. The method of claim 4, wherein in response to an item of the report, the method further includes guiding the coach to escalate care of the individual to a higher level of care beyond the coach, using a user interface of the computing device of the coach, and wherein, post-escalation of care of the individual, the method further includes transitioning care of the individual back to the coach.

8. The method of claim 7, wherein guiding the coach to escalate care of the individual to a higher level of care includes guiding the coach to inform the individual of a medication conducive to improving the adverse mental health state of the individual, using the application and a user interface of the computing device of the coach.

9. The method of claim 4, wherein in response to an item of the report indicating a critical level of suicidal ideation by the individual, the method further includes transitioning the individual from interactions with the coach to interactions with a licensed therapist using a messaging client of the application executing on the mobile device.

10. The method of claim 1, wherein generating the report includes determining a mental health state parameter derived from a mobility parameter extracted from GPS data of the supplementary dataset, and wherein generating the report includes comparing the mobility parameter to a mobility radius threshold with an associated duration threshold.

11. The method of claim 1, wherein receiving the survey dataset comprises providing to the individual, within the application executing at the mobile device, a survey derived from at least one of: a Patient Health Questionnaire-9 (PHQ-9) assessment, a Hamilton Rating Scale for Depression (HAM-D) assessment, and a Generalized Anxiety Disorder-7 (GAD-7) assessment.

12. The method of claim 1, further comprising at the computing system, generating a predictive model from a) a passive dataset derived from the log of use dataset and the supplementary dataset and b) the survey dataset; and wherein generating the report includes generating the report from an output of the predictive model.

13. The method of claim 1, wherein in response to an item of the report, the method further includes: allowing the coach to modify a treatment plan for the individual, the treatment plan at least partially accessible within the application executing at the mobile device of the individual.

14. A method for providing a therapy to an individual for an adverse mental health state, the method comprising:
transmitting, from a communication module executing on a mobile device to a computing system, a log of use dataset associated with communication behavior of the individual during a time period, wherein the log of use dataset includes at least one of a phone calling component and a text messaging component;
at the computing system, receiving a supplementary dataset characterizing activity of the individual in association with the time period;
within an application executing at the mobile device, generating a survey dataset upon retrieving responses provided by the individual to at least one of a set of surveys, associated with a set of time points of the time period;
within the application executing at the mobile device, presenting the individual with an option to communicate with a therapeutic entity;
in response to at least one of: an analysis of the supplementary dataset and the survey dataset, and election of the option by the individual, enabling a communicable link between the mobile device and a therapeutic entity communication device; and
by way of the communicable link, establishing a period of communication between the individual and the therapeutic entity for administration of the therapy to the individual for improvement of the adverse mental health state.

15. The method of claim 14, wherein presenting the individual with an option to communicate with the therapeutic entity includes presenting the individual with a set of therapeutic entities and receiving a selection of one of the set of therapeutic entities within the application of the mobile device.

16. The method of claim 14, wherein presenting the individual with an option to communicate with a therapeutic entity comprises: generating a comparison between a mental health state parameter and a critical threshold in the analysis, and automatically promoting a period of communication between the individual and the therapeutic entity in response to the comparison.

17. The method of claim 14, further comprising: after the period of communication, prompting each of the individual and the therapeutic entity to provide feedback pertaining the period of communication using the application of the mobile device and the therapeutic entity communication device, and receiving the feedback at the computing system.

18. The method of claim 17, further comprising: determining a set of communication features upon processing feedback from the period of communication; and generating a matching model from the set of communication features that identifies appropriate matches between the therapeutic entity and subsequent individuals electing periods of communication.

19. The method of claim 14, wherein generating the analysis includes determining a mental health state parameter derived from a mobility parameter extracted from GPS data of the supplementary dataset, and wherein generating the report includes comparing the mobility parameter to a mobility radius threshold with an associated duration threshold.

20. The method of claim 14, further including receiving an input, indicative of a self-assessed psychological state of the individual, by the individual at the mobile device, and providing information derived from the input to the therapeutic entity prior to the period of communication.

21. The method of claim 20, wherein establishing the period of communication comprises automatically establishing the period of communication in response to the input and election of the option to communicate with a therapeutic entity by the individual.

22. The method of claim 14, wherein receiving the supplementary dataset includes extracting a mobility radius associated with at least one time point of the time period and derived from global positioning sensors of the mobile device, and establishing the period of communication based on a reduction in the mobility radius determined using the computing system.

23. The method of claim 14, further including at the computing system, generating a predictive model from a) a passive dataset derived from the log of use dataset and the supplementary dataset and b) the survey dataset; and wherein enabling the communicable link is based on an output of the predictive model.

* * * * *

UNITED STATES PATENT AND TRADEMARK OFFICE
CERTIFICATE OF CORRECTION

PATENT NO. : 10,276,260 B2  
APPLICATION NO. : 15/005923  
DATED : April 30, 2019  
INVENTOR(S) : Sai Moturu et al.

Page 1 of 1

It is certified that error appears in the above-identified patent and that said Letters Patent is hereby corrected as shown below:

In the Claims

Column 32, Line 59, after "report", delete "to the"

Signed and Sealed this
Twenty-fifth Day of February, 2020

Andrei Iancu
*Director of the United States Patent and Trademark Office*